US008604108B2

(12) United States Patent
Hill et al.

(10) Patent No.: US 8,604,108 B2
(45) Date of Patent: Dec. 10, 2013

(54) METHOD FOR PRODUCING MONO-HYDROXYFUNCTIONALIZED DIALKYLPHOSPHINIC ACIDS AND ESTERS AND SALTS THEREOF BY MEANS OF ACROLEINS AND USE THEREOF

(75) Inventors: Michael Hill, Cologne (DE); Werner Krause, Huerth (DE); Martin Sicken, Cologne (DE)

(73) Assignee: Clariant Finance (BVI) Limited, Tortola (VG)

( * ) Notice: Subject to any disclaimer, the term of this patent is extended or adjusted under 35 U.S.C. 154(b) by 163 days.

(21) Appl. No.: 13/121,903

(22) PCT Filed: Oct. 6, 2009

(86) PCT No.: PCT/EP2009/007125
§ 371 (c)(1),
(2), (4) Date: Mar. 30, 2011

(87) PCT Pub. No.: WO2010/051885
PCT Pub. Date: May 14, 2010

(65) Prior Publication Data
US 2011/0224339 A1    Sep. 15, 2011

(30) Foreign Application Priority Data
Nov. 5, 2008    (DE) .................. 10 2008 055 914

(51) Int. Cl.
*C08K 5/5313*    (2006.01)
(52) U.S. Cl.
USPC ............. 524/133; 558/87; 558/104; 556/174; 556/20
(58) Field of Classification Search
USPC ........................................................ 524/133
See application file for complete search history.

(56) References Cited

U.S. PATENT DOCUMENTS

| | | | |
|---|---|---|---|
| 3,345,432 A | 10/1967 | Gillham et al. | |
| 3,784,628 A * | 1/1974 | Lambert | 585/834 |
| 3,784,638 A | 1/1974 | Lambert | |
| 3,875,263 A | 4/1975 | Herwig et al. | |
| 3,939,050 A | 2/1976 | Kleiner et al. | |
| 3,941,752 A | 3/1976 | Kleiner et al. | |
| 3,962,194 A | 6/1976 | Bollert et al. | |
| 4,001,352 A | 1/1977 | Kleiner et al. | |
| 4,035,343 A | 7/1977 | Bollert et al. | |
| 4,069,245 A | 1/1978 | Dursch et al. | |
| 4,069,247 A | 1/1978 | Kleiner | |
| 4,079,049 A | 3/1978 | Ramsay et al. | |
| 4,168,267 A | 9/1979 | Petrillo | |
| 4,235,991 A | 11/1980 | Digiacomo | |
| 4,337,201 A | 6/1982 | Petrillo | |
| 4,374,131 A | 2/1983 | Petrillo | |
| 4,381,297 A | 4/1983 | Karanewsky et al. | |
| 4,414,352 A * | 11/1983 | Cohen et al. | 524/443 |
| 4,427,665 A | 1/1984 | Karanewsky et al. | |
| 4,555,506 A | 11/1985 | Karanewsky et al. | |
| 4,594,199 A | 6/1986 | Thottathil et al. | |
| 4,602,092 A | 7/1986 | Thottathil et al. | |
| 4,634,689 A | 1/1987 | Witkowski et al. | |
| 5,013,863 A | 5/1991 | Baylis et al. | |
| 5,153,347 A | 10/1992 | Lloyd | |
| 5,190,934 A | 3/1993 | Mickel et al. | |
| 5,229,379 A | 7/1993 | Marescaux et al. | |
| 5,391,743 A | 2/1995 | Ebitino et al. | |
| 5,407,922 A | 4/1995 | Marescaux et al. | |
| 5,545,631 A | 8/1996 | Marescaux | |
| 5,739,123 A | 4/1998 | Norcini et al. | |
| 5,780,534 A | 7/1998 | Kleiner et al. | |

(Continued)

FOREIGN PATENT DOCUMENTS

| | | |
|---|---|---|
| AT | 243952 | 12/1965 |
| DE | 1494922 | 6/1969 |

(Continued)

OTHER PUBLICATIONS

PCT International Search Report for PCT/EP2009/007145, mailed Jan. 25, 2010.

(Continued)

*Primary Examiner* — Doris Lee
(74) *Attorney, Agent, or Firm* — Anthony A. Bisulca

(57) ABSTRACT

The invention relates to a method for producing mono-hydroxyfunctionalized dialkylphosphinic acids and esters and salts thereof by means of acroleins, characterized in that a) a phosphinic acid source (I) is reacted with olefins (IV) to yield an alkylphosphonic acid, salt or ester (II) thereof in the presence of a catalyst A, b) the thus obtained alkylphosphonic acid, salt or ester (II) thereof is reacted with compounds of formula (V) to yield a mono-functionalized dialkylphosphinic acid derivatives (IV) in the presence of a catalyst B, and c) the thus obtained mono-functionalized dialkylphosphinic acid derivatives (VI) are reacted to yield a mono-hydroxyfunctionalized dialkylphosphinic acid derivative (III) in the presence of a catalyst C, wherein $R^1$, $R^2$, $R^3$, $R^4$, $R^5$, $R^6$, $R^7$ are the same or different and stand independently of each other, among other things, for H, $C_1$-$C_{18}$ alkyl, $C_6$-$C_{18}$ aryl, $C_6$-$C_6$-$C_{18}$ aralkyl, $C_6$-$C_{18}$ alkylaryl, and X stands for H, $C_1$-$C_{18}$ alkyl, $C_6$-$C_{18}$ aryl, $C_6$-$C_{18}$ aralkyl, $C_6$-$C_{18}$ alkylaryl, Mg, Ca, Al, Sb, Sn, Ge, Ti, Fe, Zr, Zn, Ce, Bi, Sr, Mn, Cu, Ni, Li, Na, K and/or a protonized nitrogen base, and the catalyst A and C are formed by transition metals and/or transition metal compounds and/or catalyst systems composed of a transition metal and/or a transition metal compound and at least one ligand, and catalyst B is formed by compounds forming peroxides and/or peroxo compounds and/or azo compounds and/or alkali metals and/or alkaline earth metals, alkali hydrides, alkaline earth hydrides and/or alkali alcoholates and alkaline earth alcoholates.

11 Claims, No Drawings

(56) References Cited

U.S. PATENT DOCUMENTS

| | | | |
|---|---|---|---|
| 6,013,707 | A | 1/2000 | Kleiner et al. |
| 6,090,968 | A | 7/2000 | Horold et al. |
| 6,214,812 | B1 | 4/2001 | Karpeisky |
| 6,355,832 | B1 | 3/2002 | Weferling et al. |
| 6,384,022 | B1 | 5/2002 | Jackson et al. |
| 6,569,974 | B1 | 5/2003 | Sicken et al. |
| 6,727,335 | B2 | 4/2004 | Sicken et al. |
| 6,855,757 | B2 | 2/2005 | Horold et al. |
| 7,446,140 | B2 | 11/2008 | Bauer |
| 7,473,794 | B2 | 1/2009 | Wehner et al. |
| 7,485,745 | B2 | 2/2009 | Maas et al. |
| 7,749,985 | B2 | 7/2010 | Gallop et al. |
| 7,829,736 | B2 | 11/2010 | Wehner et al. |
| 8,084,518 | B2 | 12/2011 | Bauer |
| 8,097,753 | B2 | 1/2012 | Maas et al. |
| 2002/0187977 | A1 | 12/2002 | Pearlman et al. |
| 2003/0171466 | A1 | 9/2003 | Horold et al. |
| 2003/0216533 | A1 | 11/2003 | Sicken et al. |
| 2005/0187196 | A1 | 8/2005 | Madrid et al. |
| 2006/0084734 | A1 | 4/2006 | Bauer et al. |
| 2006/0194973 | A1 | 8/2006 | Gainer et al. |
| 2006/0264654 | A1 | 11/2006 | Wehner et al. |
| 2007/0210288 | A1 | 9/2007 | Maas et al. |
| 2007/0213436 | A1 | 9/2007 | Maas et al. |
| 2007/0213563 | A1 | 9/2007 | Maas et al. |
| 2008/0183009 | A1 | 7/2008 | Wehner et al. |
| 2008/0214708 | A1 | 9/2008 | Bauer et al. |
| 2009/0286759 | A1 | 11/2009 | Gallop et al. |
| 2010/0093239 | A1 | 4/2010 | Bauer et al. |
| 2011/0201732 | A1 | 8/2011 | Hill et al. |
| 2011/0201733 | A1 | 8/2011 | Hill et al. |
| 2011/0213052 | A1 | 9/2011 | Hill et al. |
| 2011/0213059 | A1 | 9/2011 | Hill et al. |
| 2011/0213060 | A1 | 9/2011 | Hill et al. |
| 2011/0213061 | A1 | 9/2011 | Hill et al. |
| 2011/0213062 | A1 | 9/2011 | Hill et al. |
| 2011/0213078 | A1 | 9/2011 | Hill et al. |
| 2011/0213079 | A1 | 9/2011 | Hill et al. |
| 2011/0213080 | A1 | 9/2011 | Hill et al. |
| 2011/0224340 | A1 | 9/2011 | Hill et al. |
| 2011/0237720 | A1 | 9/2011 | Hill et al. |
| 2011/0237721 | A1 | 9/2011 | Hill et al. |
| 2011/0237722 | A1 | 9/2011 | Hill et al. |
| 2011/0245385 | A1 | 10/2011 | Hill et al. |
| 2011/0245386 | A1 | 10/2011 | Hill et al. |
| 2011/0251310 | A1 | 10/2011 | Hill et al. |
| 2011/0251314 | A1 | 10/2011 | Hill et al. |
| 2011/0251315 | A1 | 10/2011 | Hill et al. |
| 2011/0275744 | A1 | 11/2011 | Hill et al. |
| 2011/0281983 | A1 | 11/2011 | Hill et al. |
| 2012/0064790 | A1 | 3/2012 | Bauer et al. |

FOREIGN PATENT DOCUMENTS

| | | |
|---|---|---|
| DE | 2236036 | 2/1974 |
| DE | 2236037 | 2/1974 |
| DE | 2302523 | 2/1974 |
| DE | 2344332 | 3/1975 |
| DE | 2441878 | 3/1976 |
| DE | 2623775 | 12/1976 |
| DE | 2942781 | 4/1980 |
| DE | 10153780 | 11/2002 |
| DE | 19912920 | 9/2009 |
| EP | 00858391 | 8/1983 |
| EP | 0319482 | 6/1989 |
| EP | 0463560 | 1/1992 |
| EP | 0699708 | 3/1996 |
| EP | 0906915 | 4/1999 |
| EP | 0969008 | 1/2000 |
| EP | 1203770 | 5/2002 |
| EP | 1369422 | 12/2003 |
| EP | 1607400 | 12/2005 |
| EP | 1693403 | 8/2006 |
| EP | 1832594 | 9/2007 |
| EP | 1832595 | 9/2007 |
| EP | 1832596 | 9/2007 |
| EP | 1905776 | 4/2008 |
| GB | 1045684 | 10/1966 |
| JP | 05230085 | 9/1993 |
| WO | WO 99/28327 | 6/1999 |
| WO | WO 01/42252 | 6/2001 |
| WO | WO 0157050 | 8/2001 |
| WO | WO 02/100871 | 12/2002 |
| WO | WO 2005/014604 | 2/2005 |
| WO | WO 2005/032494 | 4/2005 |
| WO | WO 2005/044830 | 5/2005 |
| WO | WO 2007/052169 | 5/2007 |
| WO | WO 2008/033572 | 3/2008 |
| WO | WO 2008/043499 | 4/2008 |

OTHER PUBLICATIONS

English Translation of the PCT International Preliminary Report on Patentability PCT/EP2009/007145 mailed Jun. 30, 2011.

English abstract for JP 05230085, Sep. 7, 1993.

Russian Journal of General Chemistry (translation of Zhurnal Obshchei Khimii), 74(6) pp. 864-872; XP002561442 (2004).

PCT International Search Report for PCT/EP2009/007123, mailed Jan. 29, 2010.

English Translation of the PCT International Preliminary Report on Patentability PCT/EP2009/007123 mailed May 19, 2011.

Montchamp; "Recent advances in phosphorus-carbon bond formation: synthesis of H-phosphinic acid derivatives from hypophosphus compounds" Journal of Organometallic Chemistry Elsevier-Sequoua S.A. Lausanne, CH, vol. 690; pp. 2388-2406; XP004877374 (May 16, 2005).

Sylvine Deprele et al. "Palladium-Catalyzed Hydrophosphinylation of Alkenes and Alkynes;" Journal of the American Chemical Society, American Chemical Society, Washington DC, US vol. 124, No. 32 p. 9387, XP002500862 (Jan. 1, 2002).

Bravo-Altamirano et al.: "A Novel Approach to Phosphinic Acids from Hypophosphorus Acid;" Tetrahedron Letters, Elsevier, Amsterdam, NL vol. 48, No. 33, pp. 5755-5759, XP022163552 (Jul. 19, 2007).

Sylvine Deprele et al.: "Environmentally Benign Synthesis of H-Phosphinic Acids Using a Water Tolerant, Recyclable Polymer-Supported Catalyst;" Organic Letters, American Chemical Society, US, vol. 6, No. 21, pp. 3805-3808 XP002500861 (Jan. 1, 2004).

Patrice Ribiere et al: "NiCL2-Catalyzed Hydrophosphinylation;" Journal of Organic Chemistry, American Chemical Society, Easton, US, vol. 70, No. 10, pp. 4064-4072, XP002530191 (Jan. 1, 2005).

Courdray L. et al.: "Allylic Phosphinates via Pd-Catalyzed Allylation of H-Phosphinic Acids with Allylic Alcohols;"Organic letters, vol. 10, No. 6, pp. 1123-1126 XP002561368 (Feb. 21, 2008).

Mastalerz: Synthesis of some ethylene-(P,P'-Dialkyl)-Diphosphic Acids as new Potential Antimetabolites of Succinic Acid; Roczniki Chemii Ann. Soc. Chim. Polonorum, vol. 38 pp. 61-66 XP 009126234 (1964).

Kurdyumova et al.: "Synthesis of Phosphinic Acids from Hypophosphites I Acrylates as an Unsaturated Component;" Russian Journal of General Chemistry (Translation of Zhurnal Obshchei Khimii (1997), 67(12) pp. 1852-1856 (Apr. 25, 1997).

Houben-Weyl, vol. 1211, pp. 258-259 (Apr. 22, 1963).

Houben-Weyl, vol. 1211, p. 306 (Apr. 22, 1963).

English abstract of Khairullin et al,"Reaction of chlorides of acids of trivalent phosphorus with conjugated systems I. Reaction of ethylphosphonous dichloride with alpha-beta-unstaturated acids" Zh. Obshch. Khimii. 36, pp. 289-296 (1966).

PCT International search report for PCT/EP2009/007124, mailed Feb. 22, 2010.

PCT International Preliminary Report on Patentability for PCT/EP2009/007124, mailed May 19, 2011.

Piotr Majewski: "A New Method for the Preparation of Bis(1-hydroxyalkyl)-phosphinic Acids;"Synthesis, vol. 6, pp. 555-557, XP002558292 (1987).

(56) References Cited

OTHER PUBLICATIONS

Hung Kuei Lin et al.: "Competitive inhibition of interfacial catalysis by phospholipase A2: differential interaction of inhibitors with the vesicle interface a controlling factor of inhibitor potency" J. Am. Chem. Soc, vol. 115, No. 10, 1993, pp. 3932-3942 XP009126627 (1993).
Kallinowsky G. et al.: "C13 Nuclear Magnetic Resonance Study of Some Phosphinolipids: Assignments and Conformational Studies;" Magnetic Resonance in Chemistry, vol. 27, No. 7, pp. 647-652 XP002558647 (1989).
PCT International Search Report for PCT/EP2009/007125, mailed Feb. 22, 2010.
English translation of PCT International Preliminary Report on Patentability for PCT/EP2009/007125, mailed May 19, 2011.
PCT International search report for PCT/EP2009/007126, mailed Sep. 2, 2010.
English translation of PCT International Preliminary Report on Patentability for PCT/EP2009/007126, mailed May 19, 2011.
Froestl W. et al.: "Phosphinic Acid Analogues of Gaba. 2. Selective, Orally Acitive Gabab Antagonists," Journal of Medicinal Chemistry, American Chemical Society, Washington, US, vol. 38, No. 17, pp. 3313-3331, XP000999491 (Jan. 1, 1995).
PCT International Preliminary Report on Patentability for PCT/EP2009/007127, mailed Jan. 18, 2010.
English translation of PCT International Preliminary Report on Patentability for PCT/EP2009/007127, mailed May 19, 2011.
PCT International Preliminary Report on Patentability for PCT/EP2009/007128, mailed Jan. 27, 2010.
English translation of PCT International Preliminary Report on Patentability for PCT/EP2009/007128, mailed May 19, 2011.
PCT International Preliminary Report on Patentability for PCT/EP2009/007129, mailed Feb. 22, 2010.
English translation of PCT International Preliminary Report on Patentability for PCT/EP2009/007129, mailed May 19, 2011.
PCT International Preliminary Report on Patentability for PCT/EP2009/007130, mailed Apr. 29, 2010.
English translation of PCT International Preliminary Report on Patentability for PCT/EP2009/007130, mailed May 19, 2011.
Nifant'ev et al.: "Reactions of acetylenes with hypophosphorous aand phosphous acids;" Journal of General Chemistry USSR Consultants Bureau, New York, NY, US vol. 56 No. 4 pp. 680-688 XP002165520 (Sep. 20, 1986).
English Abstract for DE 2344332, Mar. 27, 1975.
Kabachnik et al.: "Synthesis and properties of some ethylenepiphosphoryl compounds," Russian Chemical Bulletin, vol. 23, No. 10 p. 2205 XP002557075 (1974).
Saratovskikh I. et al.: "Phosphorus-containing Aminocarboxylic Acids: XIV. Synthesis of Analogs of [alpha]-Substituted Glutamic Acid" Ruddian Journal of General Chemistry Nauka/Interperiodica, Mo, vol. 75, No. 7 pp. 1077-1084 XP019301159 (Jul. 1, 2005).
Chemical Abstracts Service, Columbus, Ohio, US: Gareev et al.: "Stereochemistry of a 1,3-dipolar cycloaddition of diazomethane to alpha-substituted vinylphosphoryl compounds containing a chiral phosphorus atom" XP002567581 (1979).
Chemical Abstracts Service, Columbus, Ohio, US: Raevskii et al. "Electron-donor and acceptor functions of physiologically active and model compounds. V. Calculation of the electron-donor function of phosphoryl oxygen" XP002567582 (1984).
Isabelle Abrunhosa Thomas et al.: "Alkylation of H-Phosphinate Esters under Basic Conditions;" Jounal Organic Chemistry, American Chemical Society, Easton,; US, vol. 72, No. 8 pp. 2851-2856 XP002530192 (Jan. 1, 2007).
Catherine Ruflin et al.: "Tetrakis(trimethylsilyl)hypophosphate P2O2(OTMS)4: Synthesis, reactivity and application as flame retardants," Heteroatom Chemistry, VCH publishers, Defield Beach, FL, US, vol. 18, No. 7 pp. 721-731 XP009118331 (Nov. 6, 2007).
PCT International Search Report for PCT/EP2009/007131, mailed Feb. 8, 2010.
English translation of the PCT International Preliminary Report on Patentability for PCT/EP2009/007131, mailed May 19, 2011.
PCT International Preliminary Report on Patentability for PCT/EP2009/007132, mailed Feb. 15, 2010.

English translation of PCT International Preliminary Report on Patentability for PCT/EP2009/007132, mailed May 19, 2011.
PCT International Preliminary Report on Patentability for PCT/EP2009/007133, mailed Feb. 3, 2010.
English translation of PCT International Preliminary Report on Patentability for PCT/EP2009/007133, mailed May 19, 2011.
Database Beilstein [Online] Beilstein Institute for Organic Chemistry, Frankfurt-Main, DE; XP002561148, retrived from xfire Database accession No. Reaction ID 198358, abstract (1954).
PCT International Preliminary Report on Patentability for PCT/EP2009/007134, mailed Feb. 18, 2010.
English translation of PCT International Preliminary Report on Patentability for PCT/EP2009/007134, mailed May 19, 2011.
PCT International Preliminary Report on Patentability for PCT/EP2009/007135, mailed Mar. 17, 2010.
English translation of PCT International Preliminary Report on Patentability for PCT/EP2009/007135, mailed May 26, 2011.
Bravo-Altamirano et al.: "Palladium-Catalyzed Reaction of Hypophosphorous Compounds with Allenes, Dienes, and Allylic Electrophiles: Methodology for the Synthesis of Allylic H-Phosphinates" J. Org. Chem., vol. 73, No. 6, pp. 2292-2301 XP002567417 (Feb. 15, 2008).
Nadia Valiaeva et al.: "Phosophinic Acid Pseudopeptides Analogous to Glutamyl-gamma-glutamate: Synthesis and Coupling to Pteroyl Azides Leads to Potent Inhibitors of Folypoly-gamma-glutamate Synthetase;" J. Or. Chem., vol. 66, pp. 5146-5154 XP002567418 (2001).
Yamagishi takehiro et al.: "Stereoselective Synthesis of beta-Amino-alpha-hydroxy(allyl)phosphinates and an Application to the Synthesis of a Building Block for Phosphinyl Peptides" Synlett, No. 9, pp. 1471-1474, XP 002567142 (Jan. 1, 2002).
PCT International Search Report for PCT/EP2009/007136, mailed Mar. 22, 2010.
English translation of the PCT International Preliminary Report on Patentability for PCT/EP2009/007136, mailed Jun. 16, 2011.
Database Beilstein [online] Beilstein Institute for Organic Chemistry, Frankfurt-Main, DE; Database accession No. Reaction ID 101395 XP 002567148 (1956).
PCT International Search Report for PCT/EP2009/007137, mailed Mar. 12, 2010.
English translation of the PCT International Preliminary Report on Patentability for PCT/EP2009/007137, mailed Jun. 16, 2011.
Yamagishi et al.: "Diastereoselective synthesis of beta-substituted alpha-hydroxyphosphinates through hydrophosphinylation of alpha-heteroatom-substituted aldehydes;" Tetrahedron, Elsevier Science Publishers, Amsterdam, NL., vol. 59, No. 6 pp. 767-772 XP004404933 (Feb. 3, 2003).
Database Beilstein [online] Beilstein Institute for Organic Chemistry, Frankfurt-Main, DE; Database accession No. Reaction ID 970178 XP 002571550 (1963).
PCT International Search Report for PCT/EP2009/007139, mailed Mar. 22, 2010.
English translation of the PCT International Preliminary Report on Patentability for PCT/EP2009/007139, mailed Jun. 30, 2011.
PCT International Search Report for PCT/EP2009/007140, mailed Mar. 11, 2010.
English translation of the PCT International Preliminary Report on Patentability for PCT/EP2009/007140, mailed Jun. 30, 2011.
PCT International Search Report for PCT/EP2009/008964, mailed Jul. 9, 2010.
English translation of the PCT International Preliminary Report on Patentability for PCT/EP2009/008964, mailed Jun. 30, 2011.
Alonso et al.: "Transition-Metal Catalyzed Addition of Heteroatom-Hydrogen Bonds to Alkynes;" Chem. Rev., pp. 3148-3153 XP002556525 (2004).
Pudovick et al.: "Free Radical Reaction of Addition of Partial Esters of Phosphorus Acids to Acetylenic Hydrocarbons;" J. Gen. Chem. USSR, vol. 39, No. 5, pp. 986-988 XP009126232 (1969).
Database Beilstein [online] Beilstein Institute for Organic Chemistry, Frankfurt-Main, DE; Database accession No. Reaction BRN 3110535, retrieved from xfire XP002557076 (1967).

(56) References Cited

OTHER PUBLICATIONS

Database Beilstein [Online] Beilstein Institute for Organic Chemistry, Frankfurt-Main, DE; Database accession No. Reaction BRN 8075738 XP 002557077 (1997).
PCT International Search Report for PCT/EP2009/007142, mailed Feb. 9, 2010.
English translation of PCT International Preliminary Report on Patentability for PCT/EP2009/007142, mailed Jun. 30, 2011.
English Abstract for SU 314758, Sep. 21, 1971.
Sasse K Ed—Sasse K: "Houben-Weyl Methoden der Organischen Chemie", Organische Phosphor-Verbindungen; [Methoden der Organischen Chemie], Stuttgart, G. Thieme Verlag DE, XP002500739, pp. 257-259, 261, 294-301 (Jan. 1, 1963).
"1" In: Sasse K Ed—Sasse K: "Houben-Weyl Methoden der Organischen Chemie;" Organische Phosphor-Verbindungen; [Methoden der Organischen Chemie], Stuttgart, G. Thieme Verlag, DE, p. 358, XP002564325 (Jan. 1, 1963).
Regitz:"Houben-Weyl Methoden der Organischen Chemie" Organische Phosphor-Verbindungen; [Methoden der Organischen Chemie], Stuggart, G. Thieme Verlag, DE, pp. 308-309 XP002564334 (Jan. 1, 1982).
Yamagishi et al.: "Lipase-catalyzed kinetic resolution of alpha-hydroxy-H-phosphinates" Tetrahedron Letters, Elsevier, Amsterdam, NL, vol. 45, No. 36, pp. 6713-6716 XP004556626 (Aug. 30, 2004).
Anderson et al.: "Antidiabetic agents: a new class of reversible carnitine palmitoyltrasferase I inhibitors;" J. Med. Chem., vol. 38, No. 18, pp. 3448-3450 XP002564326 (1995).
Karanewsky et al.: "Synthesis of Phosphinic Monoesters from Phosphonous Acids" Tetrahedron Letters, Elsevier, Amsterdam, NL, vol. 27, No. 16, pp. 1751-1754 XP001084930 (Jan. 1, 1986).
Issleib, et al.: "Synthese und Reaktionsverhalten der Athylen-bis-organophosphine;" Chemische Berichte, vol. 101, pp. 2197-2202 XP009126251.
PCT International Search Report for PCT/EP2009/007143, mailed Feb. 17, 2010.
English translation of the PCT International Preliminary Report on Patentability for PCT/EP2009/007143, mailed Jun. 30, 2011.
Regitz: "Houben-Weyl Methoden der Organishcen Chemie" p. 188, (Jan. 1, 1982).
Rezanka et al.: "Synthesis of a Bifunctional Monophosphinate DOTA Derivative Having a Free Carboxylate Group in the Phosphorus Side Chain;" Synthesis, Georg Thieme Verlag, Stuttgart pp. 1431-1435 XP009126087 (Sep. 1, 2008).
Database Beilstein [online] Beilstein Institute for Organic Chemistry, Frankfurt-Main, DE; Database accession No. Reaction ID 938840 XP002557780 (1962).
Diel et al.: "Organische Phosphorverbindungen 84. Herstellung Eigenschaften und Biologische Wirkung von Hydrazino-Methyl-Phosphon- und Phosphinsaeuren und Derivatin;" Phosphorus and Sulfur and the Related Elements, Gordon and Breach—Harwood Academic, CH, vol. 36, pp. 85-98 XP001105809 (Jan. 1, 1998).
Sasse K Ed—Sasse K: "Houben-Weyl Methoden der Organischen Chemie", Organische Phosphor-Verbindungen; [Methoden der Organischen Chemie], Stuttgart, G. Thieme Verlag DE, XP002557781, pp. 228-229 (Jan. 1, 1963).
Kielbasinski et al: "Enzymatic reactions in ionic liquids: lipase-catalysed kinetic resolution of racemic, P-chiral hydroxymethanephosphinates and hydroxmethylphosphine oxides;" Tetrahedron Asymmetry, Pergamon Press Ltd, Oxford, GB, vol. 13, No. 7, pp. 735-738 XP004354866 (May 2, 2002).
Maier: "Organic Phosphorus compounds 91.1 Synthesis and Properties of 1-Amino-2-Arylethylphosphinic and—Phosphinic Acids as well as Phosphine Oxides;" Phosphorus, Sulfur and Silicon and the Related Elements, Gordon and Breach Science Publishers, Amsterdam, GB, vol. 53, No. 1/04 pp. 43-67 XP000671624 (Jan. 1, 1990).
US 6,248,921, 06/2001, Weferling et al. (withdrawn)

* cited by examiner

METHOD FOR PRODUCING MONO-HYDROXYFUNCTIONALIZED DIALKYLPHOSPHINIC ACIDS AND ESTERS AND SALTS THEREOF BY MEANS OF ACROLEINS AND USE THEREOF

This invention relates to a method for producing monohydroxy-functionalized dialkylphosphinic acids, esters and salts by means of acroleins and to their use.

Hitherto there are no methods in existence for producing monohydroxy-functionalized dialkylphosphinic acids, esters and salts that are available economically and on a large industrial scale and more particularly enable a high space-time yield to be achieved. Nor are there any methods that are sufficiently effective without unwelcome halogen compounds as starting materials, nor any where the end products are easy to obtain or isolate or else obtainable in a specific and desirable manner under controlled reaction conditions (such as a transesterification for example).

We have found that this object is achieved by a method for producing monohydroxy-functionalized dialkylphosphinic acids, esters and salts, which comprises a) reacting a phosphinic acid source (I)

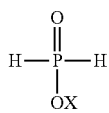
(I)

with olefins (IV)

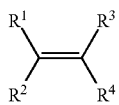
(IV)

in the presence of a catalyst A to form an alkylphosphonous acid, salt or ester (II)

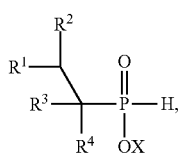
(II)

b) reacting the resulting alkylphosphonous acid, salt or ester (II) with an acrolein (V)

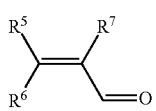
(V)

in the presence of a catalyst B to form the monofunctionalized dialkylphosphinic acid derivative (VI)

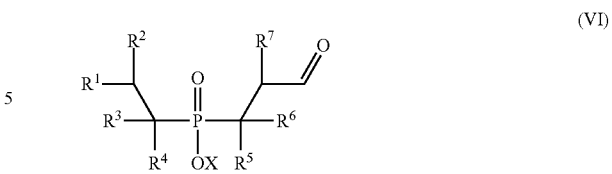
(VI)

and c) reacting the monofunctionalized dialkylphosphinic acid derivative VI with a reducing agent or in the presence of a catalyst C with hydrogen to form the monohydroxy-functionalized dialkylphosphinic acid derivative (III)

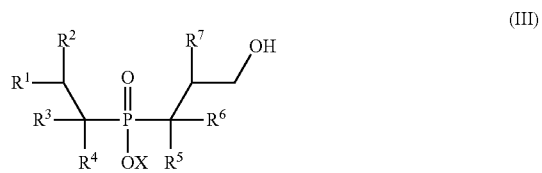
(III)

where $R^1, R^2, R^3, R^4, R^5, R^6, R^7$ are identical or different and are each independently H, $C_1$-$C_{18}$-alkyl, $C_6$-$C_{18}$-aryl, $C_6$-$C_{18}$-aralkyl, $C_6$-$C_{18}$-alkylaryl, CN, CHO, OC(O)$CH_2$CN, CH(OH)$C_2H_5$, $CH_2$CH(OH)$CH_3$, 9-anthracene, 2-pyrrolidone, $(CH_2)_m$OH, $(CH_2)_m$NH$_2$, $(CH_2)_m$NCS, $(CH_2)_m$NC(S)NH$_2$, $(CH_2)_m$SH, $(CH_2)_m$S-2-thiazoline, $(CH_2)_m$SiMe$_3$, C(O)$R^8$, $(CH_2)_m$C(O)$R^8$, CH=CH—$R^8$, CH=CH—C(O)$R^8$ and where $R^8$ is $C_1$-$C_8$-alkyl or $C_6$-$C_{18}$-aryl and m is an integer from 0 to 10 and X is H, $C_1$-$C_{18}$-alkyl, $C_6$-$C_{18}$-aryl, $C_6$-$C_{18}$-aralkyl, $C_6$-$C_{18}$-alkylaryl, $(CH_2)_k$OH, $CH_2$—CHOH—$CH_2$OH, $(CH_2)_k$O$(CH_2)_k$H, $(CH_2)_k$—CH(OH)—$(CH_2)_k$H, $(CH_2$—$CH_2$O)$_k$H, $(CH_2$—C[$CH_3$]HO)$_k$H, $(CH_2$—C[$CH_3$]HO)$_k$($CH_2$—$CH_2$O)$_k$H, $(CH_2$—$CH_2$O)$_k$($CH_2$—C[$CH_3$]HO)H, $(CH_2$—$CH_2$O)$_k$-alkyl, $(CH_2$—C[$CH_3$]HO)$_k$-alkyl, $(CH_2$—C[$CH_3$]HO)$_k$($CH_2$—$CH_2$O)$_k$-alkyl, $(CH_2$—$CH_2$O)$_k$($CH_2$—C[$CH_3$]HO)O-alkyl, $(CH_2)_k$—CH=CH$(CH_2)_k$H, $(CH_2)_k$NH$_2$, $(CH_2)_k$N[$(CH_2)_k$H]$_2$, where k is an integer from 0 to 10, and/or Mg, Ca, Al, Sb, Sn, Ge, Ti, Fe, Zr, Zn, Ce, Bi, Sr, Mn, Cu, Ni, Li, Na, K, H and/or a protonated nitrogen base and the catalysts A and C comprise transition metals and/or transition metal compounds and/or catalyst systems composed of a transition metal and/or transition metal compound and at least one ligand, and the catalyst B comprises peroxide-forming compounds and/or peroxo compounds and/or comprises azo compounds and/or comprises alkali metal hydrides and/or alkaline earth metal hydrides and/or alkai metal alkoxides and/or alkaline earth metal alkoxides.

Preferably, the monohydroxy-functionalized dialkylphosphinic acid, its salt or ester (III) obtained after step c) is subsequently reacted in a step d) with metal compounds of Mg, Ca, Al, Sb, Sn, Ge, Ti, Fe, Zr, Zn, Ce, Bi, Sr, Mn, Li, Na, K and/or a protonated nitrogen base to form the corresponding monohydroxy-functionalized dialkylphosphinic acid salts (III) of these metals and/or of a nitrogen compound.

Preferably, the alkylphosphonous acid, salt or ester (II) obtained after step a) and/or the monofunctionalized dialkylphosphinic acid, salt or ester (VI) obtained after step b) and/or the monohydroxy-functionalized dialkylphosphinic acid, salt or ester (III) obtained after step c) and/or the particular resulting reaction solution thereof are esterified with an alkylene oxide or an alcohol M-OH and/or M'-OH, and the respectively resulting alkylphosphonous ester (II) and/or mono-functionalized dialkylphosphinic ester (VI) and/or monohydroxy-functionalized dialkylphosphinic ester (III) are subjected to the further reaction steps b), c) or d).

Preferably, the groups $C_6$-$C_{18}$-aryl, $C_6$-$C_{18}$-aralkyl and $C_6$-$C_{18}$-alkylaryl are substituted with $SO_3X_2$, —C(O)CH$_3$, OH, CH$_2$OH, CH$_3$SO$_3X_2$, PO$_3X_2$, NH$_2$, NO$_2$, OCH$_3$, SH and/or OC(O)CH$_3$.

Preferably, $R^1$, $R^2$, $R^3$, $R^4$, $R^5$, $R^6$, $R^7$ are identical or different and are each independently H, methyl, ethyl, n-propyl, isopropyl, n-butyl, isobutyl, tert-butyl and/or phenyl.

Preferably, X is H, Ca, Mg, Al, Zn, Ti, Fe, Ce, methyl, ethyl, n-propyl, isopropyl, n-butyl, isobutyl, tert-butyl, phenyl, ethylene glycol, propyl glycol, butyl glycol, pentyl glycol, hexyl glycol, allyl and/or glycerol.

Preferably m=1 to 10 and k=2 to 10.

Preferably, the catalyst system A or C is formed by reaction of a transition metal and/or of a transition metal compound and at least one ligand.

Preferably, the transition metals and/or transition metal compounds comprise such from the seventh and eighth transition groups.

Preferably, the transition metals and/or transition metal compounds comprise rhodium, nickel, palladium, platinum, ruthenium.

Preferably, the catalyst B comprises hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-t-butyl peroxide and/or peroxodisulfuric acid and/or comprises azobisisobutyronitrile, 2,2'-azobis(2-amidinopropane)dihydrochloride and/or 2,2'-azobis(N,N'-dimethyleneisobutyramidine)dihydrochloride and/or comprises lithium, lithium hydride, lithium aluminohydride, methyllithium, butyllithium, t-butyllithium, lithium diisopropylamide, sodium, sodium hydride, sodium borohydride, sodium methoxide, sodium ethoxide, sodium butoxide, potassium methoxide, potassium ethoxide and/or potassium butoxide.

Preferably, the acroleins (V) comprise 2-propenal, 2-methyl-2-propenal, 2-phenyl-2-propenal, 3-phenyl-2-propenal, 2-methyl-3-phenyl-2-propenal, 2-butenal, 2-methyl-2-butenal, 2-phenyl-2-butenal, 3-methyl-2-butenal, 2-methyl-2-butenal, 2-pentenal, 2-methyl-2-pentenal, 2-phenyl-2-pentenal, 4-methyl-2-phenyl-2-pentenal and/or 2,2-dimethyl-4-pentenal.

Preferably, the alcohol of the general formula M-OH comprises linear or branched, saturated and unsaturated, monohydric organic alcohols having a carbon chain length of $C_1$-$C_{18}$ and the alcohol of the general formula M'-OH comprises linear or branched, saturated and unsaturated polyhydric organic alcohols having a carbon chain length of $C_1$-$C_{18}$.

The present invention additionally provides for the use of monohydroxy-functionalized dialkylphosphinic acids, salts and esters obtained according to one or more of claims 1 to 11 as an intermediate for further syntheses, as a binder, as a crosslinker or accelerant to cure epoxy resins, polyurethanes and unsaturated polyester resins, as polymer stabilizers, as crop protection agents, as a therapeutic or additive in therapeutics for humans and animals, as a sequestrant, as a mineral oil additive, as a corrosion control agent, in washing and cleaning applications in electronic applications.

The present invention likewise provides for the use of monohydroxy-functionalized dialkylphosphinic acids, salts and esters (III) obtained according to one or more of claims 1 to 11 as a flame retardant, more particularly as a flame retardant for clearcoats and intumescent coatings, as a flame retardant for wood and other cellulosic products, as a reactive and/or nonreactive flame retardant for polymers, in the manufacture of flame-retardant polymeric molding materials, in the manufacture of flame-retardant polymeric molded articles and/or for flame-retardant finishing of polyester and cellulose straight and blend fabrics by impregnation.

The present invention also provides a flame-retardant thermoplastic or thermoset polymeric molding material containing 0.5% to 45% by weight of monohydroxy-functionalized dialkylphosphinic acids, salts or esters (III) obtained according to one or more of claims 1 to 11, 0.5% to 95% by weight of thermoplastic or thermoset polymer or mixtures thereof, 0% to 55% by weight of additives and 0% to 55% by weight of filler or reinforcing materials, wherein the sum total of the components is 100% by weight.

Lastly, the invention also provides flame-retardant thermoplastic or thermoset polymeric molded articles, films, threads and fibers containing 0.5% to 45% by weight of monohydroxy-functionalized dialkylphosphinic acids, salts or esters (III) obtained according to one or more of claims 1 to 11, 0.5% to 95% by weight of thermoplastic or thermoset polymer or mixtures thereof, 0% to 55% by weight of additives and 0% to 55% by weight of filler or reinforcing materials, wherein the sum total of the components is 100% by weight.

All the aforementioned reactions can also be carried out in stages; similarly, the various processing steps can also utilize the respective resulting reaction solutions.

When the monohydroxy-functionalized dialkylphosphinic acid (III) after step c) comprises an ester, an acidic or basic hydrolysis may preferably be carried out in order that the free monohydroxy-functionalized dialkylphosphinic acid or salt may be obtained.

Preferably, the monohydroxy-functionalized dialkylphosphinic acid comprises 3-(ethylhydroxyphosphinyl)-1-hydroxypropane, 3-(propylhydroxyhosphinyl)-1-hydroxypropane, 3-(i-propylhydroxyphosphinyl)-1-hydroxypropane, 3-(butylhydroxyphosphinyl)-1-hydroxypropane, 3-(sec-butylhydroxy-phosphinyl)-1-hydroxypropane, 3-(i-butylhydroxyphosphinyl)-1-hydroxypropane, 3-(2-phenylethylhydroxyphosphinyl)-1-hydroxypropane, 3-(ethylhydroxyphosphinyl)-2-methyl-1-hydroxypropane, 3-(propylhydroxy-phosphinyl)-2-methyl-1-hydroxypropane, 3-(i-propylhydroxyphosphinyl)-2-methyl-1-hydroxypropane, 3-(butylhydroxyphosphinyl)-2-methyl-1-hydroxypropane, 3-(sec-butylhydroxyphosphinyl)-2-methyl-1-hydroxypropane, 3-(i-butylhydroxy-phosphinyl)-2-methyl-1-hydroxypropane, 3-(2-phenylethylhydroxyphosphinyl)-2-methyl-1-hydroxypropane, 3-(ethylhydroxyphosphinyl)-3-phenyl-1-hydroxypropane, 3-(propylhydroxyphosphinyl)-3-phenyl-1-hydroxypropane, 3-(i-propylhydroxyphosphinyl)-3-phenyl-1-hydroxypropane, 3-(butylhydroxyphosphinyl)-3-phenyl-1-hydroxypropane, 3-(sec-butylhydroxyphosphinyl)-3-phenyl-1-hydroxypropane, 3-(i-butylhydroxyphosphinyl)-3-phenyl-1-hydroxypropane, 3-(2-phenylethyl-hydroxyphosphinyl)-3-phenyl-1-hydroxypropane, the esters comprise methyl, ethyl; i-propyl; butyl, phenyl; 2-hydroxyethyl, 2-hydroxypropyl, 3-hydroxypropyl, 4-hydroxybutyl and/or 2,3-dihydroxypropyl esters of the aforementioned monohydroxy-functionalized dialkylphosphinic acids and the salts comprise an aluminum(III), calcium (II), magnesium(II), cerium(III), titanium(IV) and/or zinc(II) salt of the aforementioned monohydroxy-functionalized dialkylphosphinic acids.

Preferably, the transition metals for catalyst A comprise elements of the seventh and eighth transition groups (a metal of group 7, 8, 9 or 10, in modern nomenclature), for example rhenium, ruthenium, cobalt, rhodium, iridium, nickel, palladium and platinum.

Preference for use as source of the transition metals and transition metal compounds is given to their metal salts. Suitable salts are those of mineral acids containing the anions fluoride, chloride, bromide, iodide, fluorate, chlorate, bromate, iodate, fluorite, chlorite, bromite, iodite, hypofluorite, hypochlorite, hypobromite, hypoiodite, perfluorate, perchlorate, perbromate, periodate, cyanide, cyanate, nitrate, nitride, nitrite, oxide, hydroxide, borate, sulfate, sulfite, sulfide, persulfate, thiosulfate, sulfamate, phosphate, phosphite, hypophosphite, phosphide, carbonate and sulfonate, for example methanesulfonate, chlorosulfonate, fluorosulfonate, trifluoromethanesulfonate, benzenesulfonate, naphthylsulfonate, toluenesulfonate, t-butylsulfonate, 2-hydroxypropanesulfonate and sulfonated ion exchange resins; and/or organic salts, for example acetylacetonates and salts of a carboxylic acid having up to 20 carbon atoms, for example formate, acetate, propionate, butyrate, oxalate, stearate and citrate including halogenated carboxylic acids having up to 20 carbon atoms, for example trifluoroacetate, trichloroacetate.

A further source of the transition metals and transition metal compounds is salts of the transition metals with tetraphenylborate and halogenated tetraphenylborate anions, for example perfluorophenylborate.

Suitable salts similarly include double salts and complex salts consisting of one or more transition metal ions and independently one or more alkali metal, alkaline earth metal, ammonium, organic ammonium, phosphonium and organic phosphonium ions and independently one or more of the abovementioned anions. Examples of suitable double salts are ammonium hexachloropalladate and ammonium tetrachloropalladate.

Preference for use as a source of the transition metals is given to the transition metal as an element and/or a transition metal compound in its zerovalent state.

Preferably, the transition metal salt is used as a metal, or as an alloy with further metals, in which case boron, zirconium, tantalum, tungsten, rhenium, cobalt, iridium, nickel, palladium, platinum and/or gold is preferred here. The transition metal content in the alloy used is preferably 45-99.95% by weight.

Preferably, the transition metal is used in microdisperse form (particle size 0.1 mm-100 μm).

Preferably, the transition metal is used supported on a metal oxide such as, for example, alumina, silica, titanium dioxide, zirconium dioxide, zinc oxide, nickel oxide, vandium oxide, chromium oxide, magnesium oxide, Celite®, diatomaceous earth, on a metal carbonate such as, for example, barium carbonate, calcium carbonate, strontium carbonate, on a metal sulfate such as, for example, barium sulfate, calcium sulfate, strontium sulfate, on a metal phosphate such as, for example, aluminum phosphate, vanadium phosphate, on a metal carbide such as, for example, silicone carbide, on a metal aluminate such as, for example, calcium aluminate, on a metal silicate such as, for example, aluminum silicate, chalks, zeolites, bentonite, montmorillonite, hectorite, on functionalized silicates, functionalized silica gels such as, for example, SiliaBond®, QuadraSil™, on functionalized polysiloxanes such as, for example, Deloxan®, on a metal nitride, on carbon, activated carbon, mullite, bauxite, antimonite, scheelite, perovskite, hydrotalcite, heteropolyanions, on functionalized and unfunctionalized cellulose, chitosan, keratin, heteropolyanions, on ion exchangers such as, for example, Amberlite™, Amberjet™, Ambersep™, Dowex®, Lewatit®, ScavNet®, on functionalized polymers such as, for example, Chelex®, QuadraPure™, Smopex®, PolyOrgs®, on polymer-bound phosphanes, phosphane oxides, phosphinates, phosphonates, phosphates, amines, ammonium salts, amides, thioamides, ureas, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silica and/or dendrimers.

Suitable sources for the metal salts and/or transition metals likewise preferably include their complex compounds. Complex compounds of the metal salts and/or transition metals are composed of the metal salts/transition metals and one or more complexing agents. Suitable complexing agents include for example olefins, diolefins, nitriles, dinitriles, carbon monoxide, phosphines, diphosphines, phosphites, diphosphites, dibenzylideneacetone, cyclopentadienyl, indenyl or styrene. Suitable complex compounds of the metal salts and/or transition metals may be supported on the abovementioned support materials.

The proportion in which the supported transition metals mentioned are present is preferably in the range from 0.01% to 20% by weight, more preferably from 0.1% to 10% by weight and even more preferably from 0.2% to 5% by weight, based on the total mass of the support material.

Suitable sources for transition metals and transition metal compounds include for example palladium, platinum, nickel, rhodium; palladium platinum, nickel or rhodium, on alumina, on silica, on barium carbonate, on barium sulfate, on calcium carbonate, on strontium carbonate, on carbon, on activated carbon; platinum-palladium-gold alloy, aluminum-nickel alloy, iron-nickel alloy, lanthanide-nickel alloy, zirconium-nickel alloy, platinum-iridium alloy, platinum-rhodium alloy; Raney® nickel, nickel-zinc-iron oxide; palladium(II) chloride, palladium(II) bromide, palladium(II) iodide, palladium (II) fluoride, palladium(II) hydride, palladium(II) oxide, palladium(II) peroxide, palladium(II) cyanide, palladium(II) sulfate, palladium(II) nitrate, palladium(II) phosphide, palladium(II) boride, palladium(II) chromium oxide, palladium (II) cobalt oxide, palladium(II) carbonate hydroxide, palladium(II) cyclohexane butyrate, palladium(II) hydroxide, palladium(II) molybdate, palladium(II) octanoate, palladium (II) oxalate, palladium(II) perchlorate, palladium(II) phthalocyanine, palladium(II) 5,9,14,18,23,27,32,36-octabutoxy-2,3-naphthalocyanine, palladium(II) sulfamate, palladium (II) perchlorate, palladium(II) thiocyanate, palladium(II) bis (2,2,6,6-tetramethyl-3,5-heptanedionate), palladium(II) propionate, palladium(II) acetate, palladium(II) stearate, palladium(II) 2-ethylhexanoate, palladium(II) acetylacetonate, palladium(II) hexafluoroacetylacetonate, palladium(II) tetrafluoroborate, palladium(II) thiosulfate, palladium(II) trifluoroacetate, palladium(II) phthalocyaninetetrasulfonic acid tetrasodium salt, palladium(II) methyl, palladium(II) cyclopentadienyl, palladium(II) methylcyclopentadienyl, palladium(II) ethylcyclopentadienyl, palladium(II) pentamethylcyclopentadienyl, palladium(II) 2,3,7,8,12,13,17,18-octaethyl-21H,23H-porphine, palladium(II) 5,10,15,20-tetraphenyl-21H,23H-porphine, palladium(II) bis(5-[[4-(dimethylamino)phenyl]imino]-8(5H)-quinolinone), palladium(II) 2,11,20,29-tetra-tert-butyl-2,3-naphthalocyanine, palladium(II) 2,9,16,23-tetraphenoxy-29H,31H-phthalocyanine, palladium(II) 5,10,15,20-tetrakis(pentafluorophenyl)-21H,23H-porphine and the 1,4-bis(diphenyl-phosphine) butane, 1,3-bis(diphenylphosphino)propane, 2-(2'-di-tert-butyl-phosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenyl-phosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylamino-phenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof;

nickel(II) chloride, nickel(II) bromide, nickel(II) iodide, nickel(II) fluoride, nickel(II) hydride, nickel(II) oxide, nickel(II) peroxide, nickel(II) cyanide, nickel(II) sulfate, nickel(II) nitrate, nickel(II) phosphide, nickel(II) boride, nickel(II) chromium oxide, nickel(II) cobalt oxide, nickel(II) carbonate hydroxide, nickel(II) cyclohexane butyrate, nickel(II) hydroxide, nickel(II) molybdate, nickel(II) octanoate, nickel(II) oxalate, nickel(II) perchlorate, nickel(II) phthalocyanine, nickel(II) 5,9,14,18,23,27,32,36-octabutoxy-2,3-naphthalocyanine, nickel(II) sulfamate, nickel(II) perchlorate, nickel(II) thiocyanate, nickel(II) bis(2,2,6,6-tetramethyl-3,5-heptanedionate), nickel(II) propionate, nickel(II) acetate, nickel(II) stearate, nickel(II) 2-ethylhexanoate, nickel(II) acetylacetonate, nickel(II) hexafluoroacetylacetonate, nickel(II) tetrafluoroborate, nickel(II) thiosulfate, nickel(II) trifluoroacetate, nickel(II) phthalocyaninetetrasulfonic acid tetrasodium salt, nickel(II) methyl, nickel(II) cyclopentadienyl, nickel(II) methylcyclopentadienyl, nickel(II) ethylcyclopentadienyl, nickel(II) pentamethylcyclopentadienyl, nickel(II) 2,3,7,8,12,13,17,18-octaethyl-21H,23H-porphine, nickel(II) 5,10,15,20-tetraphenyl-21H,23H-porphine, nickel(II) bis(5-[[4-(dimethylamino)phenyl]imino]-8(5H)-quinolinone), nickel(II) 2,11,20,29-tetra-tert-butyl-2,3-naphthalocyanine, nickel(II) 2,9,16,23-tetraphenoxy-29H,31H-phthalocyanine, nickel(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diiso-propylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylamino-phenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof;

platinum(II) chloride, platinum(II) bromide, platinum(II) iodide, platinum(II) fluoride, platinum(II) hydride, platinum(II) oxide, platinum(II) peroxide, platinum(II) cyanide, platinium(II) sulfate, platinum(II) nitrate, platinum(II) phosphide, platinum(II) boride, platinum(II) chromium oxide, platinum(II) cobalt oxide, platinum(II) carbonate hydroxide, platinum(II) cyclohexane butyrate, platinum(II) hydroxide, platinum(II) molybdate, platinum(II) octanoate, platinum(II) oxalate, platinum(II) perchlorate, platinum(II) phthalocyanine, platinum(II) 5,9,14,18,23,27,32,36-octabutoxy-2,3-naphthalocyanine, platinum(II) sulfamate, platinum(II) perchlorate, platinum(II) thiocyanate, platinum(II) bis(2,2,6,6-tetramethyl-3,5-heptanedionate), platinum(II) propionate, platinum(II) acetate, platinium(II) stearate, platinium(II) 2-ethylhexanoate, platinium(II) acetylacetonate, platinum(II) hexafluoroacetylacetonate, platinum(II) tetrafluoroborate, platinum(II) thiosulfate, platinum(II) trifluoroacetate, platinum(II) phthalocyaninetetrasulfonic acid tetrasodium salt, platinum(II) methyl, platinum(II) cyclopentadienyl, platinum(II) methylcyclopentadienyl, platinum(II) ethylcyclopentadienyl, platinum(II) pentamethylcyclopentadienyl, platinum(II) 2,3,7,8,12,13,17,18-octaethyl-21H,23H-porphine, platinum(II) 5,10,15,20-tetraphenyl-21H,23H-porphine, platinum(II) bis(5-[[4-(dimethylamino)phenyl]imino]-8(5H)-quinolinone), platinum(II) 2,11,20,29-tetra-tert-butyl-2,3-naphthalocyanine, platinum(II) 2,9,16,23-tetraphenoxy-29H,31H-phthalocyanine, platinum(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenyl-sulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylamino-methyl)ferrocene, allyl, bis(diphenylphosphino)butane, (N-succinimidyl)bis-(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diiso-propylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof;

rhodium chloride, rhodium bromide, rhodium iodide, rhodium fluoride, rhodium hydride, rhodium oxide, rhodium peroxide, rhodium cyanide, rhodium sulfate, rhodium nitrate, rhodium phosphide, rhodium boride, rhodium chromium oxide, rhodium cobalt oxide, rhodium carbonate hydroxide, rhodium cyclohexane butyrate, rhodium hydroxide, rhodium molybdate, rhodium octanoate, rhodium oxalate, rhodium perchlorate, rhodium phthalocyanine, rhodium 5,9,14,18,23,27,32,36-octabutoxy-2,3-naphthalocyanine, rhodium sulfamate, rhodium perchlorate, rhodium thiocyanate, rhodium bis(2,2,6,6-tetramethyl-3,5-heptanedionate), rhodium propionate, rhodium acetate, rhodium stearate, rhodium 2-ethylhexanoate, rhodium acetylacetonate, rhodium hexafluoroacetylacetonate, rhodium tetrafluoroborate, rhodium thiosulfate, rhodium trifluoroacetate, rhodium phthalocyaninetetrasulfonic acid tetrasodium salt, rhodium methyl, rhodium cyclopentadienyl, rhodium methylcyclopentadienyl, rhodium ethylcyclopentadienyl, rhodium pentamethylcyclopentadienyl, rhodium 2,3,7,8,12,13,17,18-octaethyl-21H,23H-porphine, rhodium 5,10,15,20-tetraphenyl-21H,23H-porphine, rhodium bis(5-[[4-(dimethylamino)phenyl]imino]-8(5H)-quinolinone), rhodium 2,11,20,29-tetra-tert-butyl-2,3-naphthalocyanine, rhodium 2,9,16,23-tetraphenoxy-29H,31H-phthalocyanine, rhodium 5,10,15, 20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropyl-phenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenyiphosphine, 1,10-phenanthroline, 1,5-cyclooctadiene, N,N,N',N'-tetramethylethylenediamine, triphenyiphosphine, tri-o-tolylphosphine, tricyclohexylphosphine, tributylphosphine, triethyiphosphine, 2,2'-bis(diphenylphosphino)-1,1'-binaphthyl, 1,3-bis(2,6-diisopropyl-phenyl)imidazol-2-ylidene, 1,3-bis(mesityl)imidazol-2-ylidene, 1,1'-bis(diphenyl-phosphino)ferrocene, 1,2-bis(diphenylphosphino)ethane, N-methylimidazole, 2,2'-bipyridine, (bicyclo[2.2.1]hepta-2, 5-diene), bis(di-tert-butyl(4-dimethylamino-phenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof;

potassium hexachloropalladate(IV), sodium hexachloropalladate(IV), ammonium hexachloropalladate(IV), potassium tetrachloropalladate(II), sodium tetrachloropalladate (II), ammonium tetrachloropalladate(II), bromo(tri-tert-butylphosphine)palladium(I) dimer, (2-methylallyl) palladium(II) chloride dimer, bis(dibenzylideneacetone) palladium(0), tris(dibenzylideneacetone)dipalladium(0), tetrakis(triphenylphosphine)palladium(0), tetrakis(tricyclohexylphosphine)-palladium(0), bis[1,2-bis(diphenylphosphine)ethane]palladium(0), bis(3,5,3',5'-dimethoxydibenzylideneacetone)palladium(0), bis(tri-tert-butylphosphine) palladium(0), meso-tetraphenyltetrabenzoporphinepalladium, tetrakis (methyldiphenylphosphine)palladium(0), tris(3,3',3''-phophinidyne-tris(benzenesulfonato)palladium(0) nonasodium salt, 1,3-bis(2,4,6-trimethylphenyl)imidazol-2-ylidene(1,4-naphthoquinone)palladium(0), 1,3-bis(2,6-diisopropylphenyl)imidazol-2-ylidene(1,4-naphthoquinone) palladium(0) and the chloroform complex thereof;

allylnickel(II) chloride dimer, ammoniumnickel(II) sulfate, bis(1,5-cycloocta-diene)nickel(0), bis(triphenylphosphine)dicarbonylnickel(0), tetrakis(triphenyl-phosphine) nickel(0), tetrakis(triphenyl phosphite)nickel(0), potassium hexafluoronickelate(IV), potassium tetracyanonickelate(I) potassium nickel(IV) paraperiodate, dilithium tetrabromonickelate(II), potassium tetracyanonickelate(II); platinum(IV) chloride, platinum(IV) oxide, platinum(IV) sulfide, potassium hexachloroplatinate(IV), sodium hexachloroplatinate (IV), ammonium hexachloroplatinate(IV), potassium tetrachloroplatinate(II), ammonium tetrachloroplatinate(II), potassium tetracyanoplatinate(II), trimethyl(methylcyclopentadienyl)platinum(IV), cis-diammintetrachloroplatinum (IV), potassium trichloro(ethylene)platinate(II), sodium hexahydroxyplatinate(IV), tetraamineplatinum(II) tetrachloroplatinate(II), tetrabutylammonium hexachloroplatinate (IV), ethylenebis(triphenylphosphine)platinum(0), platinum (0) 1,3-divinyl-1,1,3,3-tetramethyldisiloxane, platinum(0) 2,4,6,8-tetramethyl-2,4,6,8-tetravinylcyclotetrasiloxane, tetrakis(triphenylphosphine)platinum(0), platinum octaethylporphyrine, chloroplatinic acid, carboplatin; chlorobis(ethylene)rhodium dimer, hexarhodium hexadecacarbonyl, chloro(1,5-cyclooctadiene)rhodium dimer, chloro(norbomadiene)rhodium dimer, chloro(1,5-hexadiene)rhodium dimer.

The ligands preferably comprise phosphines of the formula (VII)

$$PR^9_3 \quad (VII)$$

where the $R^9$ radicals are each independently hydrogen, straight-chain, branched or cyclic $C_1$-$C_{20}$-alkyl, $C_1$-$C_{20}$-alkylaryl, $C_2$-$C_{20}$-alkenyl, $C_2$-$C_{20}$-alkynyl, $C_1$-$C_{20}$-carboxylate, $C_1$-$C_{20}$-alkoxy, $C_1$-$C_{20}$-alkenyloxy, $C_1$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or their derivatives and/or phenyl substituted by at least one $R^{10}$, or naphthyl substituted by at least one $R^{10}$. $R^{10}$ in each occurrence is independently hydrogen, fluorine, chlorine, bromine, iodine, $NH_2$, nitro, hydroxyl, cyano, formyl, straight-chain, branched or cyclic $C_1$-$C_{20}$-alkyl, $C_1$-$C_{20}$-alkoxy, $HN(C_1$-$C_{20}$-alkyl), $N(C_1$-$C_{20}$-alkyl$)_2$, —$CO_2$—($C_1$-$C_{20}$-alkyl), —$CON(C_1$-$C_{20}$-alkyl$)_2$, —$OCO(C_1$-$C_{20}$-alkyl), $NHCO(C_1$-$C_{20}$-alkyl), $C_1$-$C_{20}$-Acyl, —$SO_3M$, —$SO_2N(R^{11})M$, —$CO_2M$, —$PO_3M_2$, —$AsO_3M_2$, —$SiO_2M$, —$C(CF_3)_2OM$ (M=H, Li, Na or K), where $R^{11}$ is hydrogen, fluorine, chlorine, bromine, iodine, straight-chain, branched or cyclic $C_1$-$C_{20}$-alkyl, $C_2$-$C_{20}$-alkenyl, $C_2$-$C_{20}$-alkynyl, $C_1$-$C_{20}$-carboxylate, $C_1$-$C_{20}$-alkoxy, $C_1$-$C_{20}$-alkenyloxy, $C_1$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or their derivatives, aryl, $C_1$-$C_{20}$-arylalkyl, $C_1$-$C_{20}$-alkylaryl, phenyl and/or biphenyl. Preferably, the $R^9$ groups are all identical.

Suitable phosphines(VII) are for example trimethylphosphine, triethylphosphine, tripropyiphosphine, triisopropylphosphine, tributylphosphine, triisobutylphosphine, triisopentylphosphine, trihexylphosphine, tricyclohexyiphosphine, trioctylphosphine, tridecylphosphine, triphenylphosphine, diphenylmethylphosphine, phenyldimethyiphosphine, tri(o-tolyl)phosphine, tri(p-tolyl) phosphine, ethyldiphenylphosphine, dicyclohexylphenylphosphine, 2-pyridyl-diphenylphosphine, bis(6-methyl-2-pyridyl)phenylphosphine, tri(p-chlorophenyl)-phosphine, tri(p-methoxyphenyl)phosphine, diphenyl(2-sulfonatophenyl)-phosphine; potassium, sodium and ammonium salts of diphenyl(3-sulfonatophenyl)phosphine, bis(4,6-dimethyl-3-sulfonatophenyl)(2,4-dimethylphenyl)phosphine, bis(3-sulfonatophenyl)phenylphosphines, tris(4,6-dimethyl-3-sulfonatophenyl)phosphines, tris (2-sulfonatophenyl)phosphines, tris(3-sulfonatophenyl) phosphines; 2-bis(diphenylphosphinoethyl) trimethylammonium iodide, 2'-dicyclohexylphosphino-2,6-dimethoxy-3-sulfonato-1,1-biphenyl sodium salt, trimethyl phosphite and/or triphenyl phosphite.

The ligands more preferably comprise bidentate ligands of the general formula $$R^9M''-Z-M''R^9 \quad (VIII).$$

In this formula, each M'' independently is N, P, As or Sb.

M'' is preferably the same in the two occurrences and more preferably is a phosphorus atom.

Each $R^9$ group independently represents the radicals described under formula (VII). The $R^9$ groups are preferably all identical.

Z is preferably a bivalent bridging group which contains at least 1 bridging atom, preferably from 2 to 6 bridging atoms.

Bridging atoms can be selected from carbon, nitrogen, oxygen, silicon and sulfur atoms. Z is preferably an organic bridging group containing at least one carbon atom. Z is preferably an organic bridging group containing 1 to 6 bridging atoms, of which at least two are carbon atoms, which may be substituted or unsubstituted.

Preferred Z groups are —$CH_2$—, —$CH_2$—$CH_2$—, —$CH_2$—$CH_2$—$CH_2$—, —$CH_2$—$CH(CH_3)$—$CH_2$—, —$CH_2$—$C(CH_3)_2$—$CH_2$—, —$CH_2$—$C(C_2H_5)$—$CH_2$—, —$CH_2$—$Si(CH_3)_2$—$CH_2$—, —$CH_2$—O—$CH_2$—, —$CH_2$—$CH_2$—$CH_2$—$CH_2$—, —$CH_2$—$CH(C_2H_5)$—$CH_2$—, —$CH_2$—CH(n-Pr)—$CH$, —$CH_2$—CH(n-Bu)-$CH_2$—, substituted or unsubstituted 1,2-phenyl, 1,2-cyclohexyl, 1,1'- or 1,2-ferrocenyl radicals, 2,2'-(1,1'-biphenyl), 4,5-xanthene and/or oxydi-2,1-phenylene radicals.

Examples of suitable bidentate phosphine ligands (VIII) are for example 1,2-bis(dimethylphosphino)ethane, 1,2-bis(diethylphosphino)ethane, 1,2-bis(dipropylphosphino)ethane, 1,2-bis(diisopropylphosphino)ethane, 1,2-bis(dibutylphosphino)ethane, 1,2-bis(di-tert-butylphosphino)ethane, 1,2-bis(dicyclohexylphosphino)ethane, 1,2-bis(diphenylphosphino)ethane; 1,3-bis(dicyclohexylphosphino)propane, 1,3-bis(diisopropylphosphino)propane, 1,3-bis(di-tert-butylphosphino)propane, 1,3-bis(diphenylphosphino)propane; 1,4-bis(diisopropylphosphino)butane, 1,4-bis(diphenylphosphino)butane; 1,5-bis(dicyclohexylphosphino)pentane; 1,2-bis(di-tert-butylphosphino)benzene, 1,2-bis(diphenylphosphino)benzene, 1,2-bis(dicyclohexylphosphino)benzene, 1,2-bis(dicyclopentylphosphino)benzene, 1,3-bis(di-tert-butylphosphino)benzene, 1,3-bis(diphenylphosphino)benzene, 1,3-bis(dicyclohexylphosphino)benzene, 1,3-bis(dicyclopentylphosphino)benzene; 9,9-dimethyl-4,5-bis(diphenylphosphino)-xanthene, 9,9-dimethyl-4,5-bis(diphenylphosphino)-2,7-di-tert-butylxanthene, 9,9-dimethyl-4,5-bis(di-tert-butylphosphino)xanthene, 1,1'-bis(diphenylphosphino)-ferrocene, 2,2'-bis(diphenylphosphino)-1,1'-binaphthyl, 2,2'-bis(di-p-tolyl-phosphino)-1,1'-binaphthyl, (oxydi-2,1-phenylene)bis(diphenylphosphine), 2,5-(diisopropylphospholano)benzene, 2,3-O-isopropylidene-2,3-dihydroxy-1,4-bis(diphenylphosphino)butane, 2,2'-bis(di-tert-butylphosphino)-1,1'-biphenyl, 2,2'-bis(dicyclohexylphosphino)-1,1'-biphenyl, 2,2'-bis(diphenylphosphino)-1,1'-biphenyl, 2-(di-tert-butylphosphino)-2'-(N,N-dimethylamino)biphenyl, 2-(dicyclohexylphosphino)-2'-(N,N-dimethylamino)biphenyl, 2-(diphenyl-phosphino)-2'-(N,N-dimethylamino)biphenyl, 2-(diphenylphosphino)ethylamine, 2-[2-(diphenylphosphino)ethyl]pyridine; potassium, sodium and ammonium salts of 1,2-bis(di-4-sulfonatophenylphosphino)benzene, (2,2'-bis[[bis(3-sulfonato-phenyl)phosphino]methyl]-4,4',7,7'-tetrasulfonato-1,1'-binapthyl, (2,2'-bis[[bis(3-sulfonatophenyl)phosphino]methyl]-5,5'-tetrasulfonato-1,1'-biphenyl, (2,2'-bis[[bis(3-sulfonatophenyl)phosphino]methyl]-1,1'-binapthyl, (2,2'-bis[[bis(3-sulfonatophenyl)phosphino]methyl]-1,1'-biphenyl, 9,9-dimethyl-4,5-bis(diphenyl-phosphino)-2,7-sulfonatoxanthene, 9,9-dimethyl-4,5-bis(di-tert-butylphosphino)-2,7-sulfonatoxanthene, 1,2-bis(di-4-sulfonatophenylphosphino)benzene, meso-tetrakis(4-sulfonatophenyl)porphine, meso-tetrakis(2,6-dichloro-3-sulfonato-phenyl)porphine, meso-tetrakis(3-sulfonatomesityl)porphine, tetrakis(4-carboxy-phenyl)porphine and 5,11,17,23-sulfonato-25,26,27,28-tetrahydroxycalix[4]arene.

Moreover, the ligands of the formula (VII) and (VIII) can be attached to a suitable polymer or inorganic substrate by the $R^9$ radicals and/or the bridging group.

The molar transition metal/ligand ratio of the catalyst system is in the range 1:0.01 to 1:100, preferably in the range from 1:0.05 to 1:10 and more preferably in the range from 1:1 to 1:4.

The reactions in the process stages a), b) c) and d) preferably take place, if desired, in an atmosphere comprising further gaseous constituents such as nitrogen, oxygen, argon, carbon dioxide for example; the temperature is in the range from −20 to 340° C., more particularly in the range from 20 to 180° C., and total pressure is in the range from 1 to 100 bar.

The products and/or the components and/or the transition metal and/or the transition metal compound and/or catalyst system and/or the ligand and/or starting materials are optionally isolated after the process stages a), b) c) and d) by distillation or rectification, by crystallization or precipitation, by filtration or centrifugation, by adsorption or chromatography or other known methods.

According to the present invention, solvents, auxiliaries and any other volatile constituents are removed by distillation, filtration and/or extraction for example.

The reactions in the process stages a), b) c) and d) are preferably carried out, if desired, in absorption columns, spray towers, bubble columns, stirred tanks, trickle bed reactors, flow tubes, loop reactors and/or kneaders.

Suitable mixing elements include for example anchor, blade, MIG, propeller, impeller and turbine stirrers, cross beaters, disperser disks, hollow (sparging) stirrers, rotor-stator mixers, static mixers, Venturi nozzles and/or mammoth pumps.

The intensity of mixing experienced by the reaction solutions/mixtures preferably corresponds to a rotation Reynolds number in the range from 1 to 1 000 000 and preferably in the range from 100 to 100 000.

It is preferable for an intensive commixing of the respective reactants etc. to be effected by an energy input in the range from 0.080 to 10 $kW/m^3$, preferably 0.30-1.65 $kW/m^3$.

During the reaction, the particular catalyst A or C is preferably homogeneous and/or heterogeneous in action. Therefore, the particular heterogeneous catalyst is effective during the reaction as a suspension or bound to a solid phase.

Preferably, the particular catalyst A or C is generated in situ before the reaction and/or at the start of the reaction and/or during the reaction.

Preferably, the particular reaction takes place in a solvent as a single-phase system in homogeneous or heterogeneous mixture and/or in the gas phase.

When a multi-phase system is used, a phase transfer catalyst may be used in addition.

The reactions of the present invention can be carried out in liquid phase, in the gas phase or else in supercritical phase. The particular catalyst A or C is preferably used in the case of liquids in homogeneous form or as a suspension, while a fixed bed arrangement is advantageous in the case of gas phase or supercritical operation.

Suitable solvents are water, alcohols, e.g. methanol, ethanol, isopropanol, n-propanol, n-butanol, isobutanol, tert-butanol, n-amyl alcohol, isoamyl alcohol, tert-amyl alcohol, n-hexanol, n-octanol, isooctanol, n-tridecanol, benzyl alcohol, etc. Preference is further given to glycols, e.g. ethylene glycol, 1,2-propanediol, 1,3-propanediol, 1,3-butanediol, 1,4-butanediol, diethylene glycol etc.; aliphatic hydrocarbons, such as pentane, hexane, heptane, octane, and petroleum ether, naphtha, kerosene, petroleum, paraffin oil, etc.; aromatic hydrocarbons, such as benzene, toluene, xylene, mesitylene, ethylbenzene, diethylbenzene, etc.; halogenated hydrocarbons, such as methylene chloride, chloroform, 1,2-dichloroethane, chlorobenzene, carbon tetrachloride, tetrabromoethylene, etc.; alicyclic hydrocarbons, such as cyclopentane, cyclohexane, and methylcyclo-hexane, etc.; ethers, such as anisole (methyl phenyl ether), tert-butyl methyl ether, dibenzyl ether, diethyl ether, dioxane, diphenyl ether, methyl vinyl ether, tetrahydrofuran, triisopropyl ether etc.; glycol ethers, such as diethylene glycol diethyl ether, diethylene glycol dimethyl ether (diglyme), diethylene glycol monobutyl ether, diethylene glycol monomethyl ether, 1,2-dimethoxyethane (DME, monoglyme), ethylene glycol monobutyl ether, triethylene glycol dimethyl ether (triglyme), triethylene glycol monomethyl ether etc.; ketones, such as acetone, diisobutyl ketone, methyl n-propyl ketone; methyl ethyl ketone, methyl isobutyl ketone etc.; esters, such as methyl formate, methyl acetate, ethyl acetate, n-propyl acetate, and n-butyl acetate, etc.; carboxylic acids, such as formic acid, acetic acid, propionic acid, butyric acid, etc. One or more of these compounds can be used, alone or in combination.

Suitable solvents also encompass the phosphinic acid sources and olefins used. These have advantages in the form of higher space-time yield.

It is preferable that the reaction be carried out under the autogenous vapor pressure of the olefin and/or of the solvent.

Preferably, $R^1$, $R^2$, $R^3$ and $R^4$ of olefin (IV) are the same or different and each is independently H, methyl, ethyl, n-propyl, isopropyl, n-butyl, isobutyl, tert-butyl and/or phenyl.

Preference is also given to using functionalized olefins such as allyl isothiocyanate, allyl methacrylate, 2-allylphenol, N-allylthiourea, 2-(allylthio)-2-thiazoline, allyltrimethylsillane, allyl acetate, allyl acetoacetate, allyl alcohol, allylamine, allylbenzene, allyl cyanide, allyl cyanoacetate, allylanisole, trans-2-pentenal, cis-2-pentenenitrile, 1-penten-3-ol, 4-penten-1-ol, 4-penten-2-ol, trans-2-hexenal, trans-2-hexen-1-ol, cis-3-hexen-1-ol, 5-hexen-1-ol, styrene, -methylstyrene, 4-methylstyrene, vinyl acetate, 9-vinylanthracene, 2-vinylpyridine, 4-vinylpyridine and 1-vinyl-2-pyrrolidone.

The partial pressure of the olefin during the reaction is preferably 0.01-100 bar and more preferably 0.1-10 bar.

The phosphinic acid/olefin molar ratio for the reaction is preferably in the range from 1:10 000 to 1:0.001 and more preferably in the range from 1:30 to 1:0.01.

The phosphinic acid/catalyst molar ratio for the reaction is preferably in the range from 1:1 to 1:0.00000001 and more preferably in the range from 1:0.01 to 1:0.000001.

The phosphinic acid/solvent molar ratio for the reaction is preferably in the range from 1:10 000 to 1:0 and more preferably in the range from 1:50 to 1:1.

One method the present invention provides for producing compounds of the formula (II) comprises reacting a phosphinic acid source with olefins in the presence of a catalyst and freeing the product (II) (alkylphosphonous acid, salts or esters) of catalyst, transition metal or transition metal compound as the case may be, ligand, complexing agent, salts and by-products.

The present invention provides that the catalyst, the catalyst system, the transition metal and/or the transition metal compound are separated off by adding an auxiliary 1 and removing the catalyst, the catalyst system, the transition metal and/or the transition metal compound by extraction and/or filtration.

The present invention provides that the ligand and/or complexing agent is separated off by extraction with auxiliary 2 and/or distillation with auxiliary 2.

Auxiliary 1 is preferably water and/or at least one member of the group of metal scavengers. Preferred metal scavengers are metal oxides, such as aluminum oxide, silicon dioxide, titanium dioxide, zirconium dioxide, zinc oxide, nickel oxide, vanadium oxide, chromium oxide, magnesium oxide, Celite®, kieselguhr; metal carbonates, such as barium carbonate, calcium carbonate, strontium carbonate; metal sulfates, such as barium sulfate, calcium sulfate, strontium sulfate; metal phosphates, such as aluminum phosphate, vanadium phosphate, metal carbides, such as silicone carbide; metal aluminates, such as calcium aluminate; metal silicates, such as aluminum silicate, chalks, zeolites, bentonite, montmorillonite, hectorite; functionalized silicates, functionalized silica gels, such as SiliaBond®, QuadraSil™; functionalized polysiloxanes, such as Deloxan®; metal nitrides, carbon, activated carbon, mullite, bauxite, antimonite, scheelite, perovskite, hydrotalcite, functionalized and unfunctionalized cellulose, chitosan, keratin, heteropolyanions, ion exchangers, such as Amberlite™, Amberjet™, Ambersep™, Dowex®, Lewatit®, ScavNet®; functionalized polymers, such as Chelex®, QuadraPure™, Smopex®, PolyOrgs®; polymer-bound phosphanes, phosphane oxides, phosphinates, phosphonates, phosphates, amines, ammonium salts, amides, thioamides, urea, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silicon dioxide, and/or dendrimers.

It is preferable that the amounts added of auxiliary 1 correspond to 0.1-40% by weight loading of the metal on auxiliary 1.

It is preferable that auxiliary 1 be used at temperatures of from 20 to 90° C.

It is preferable that the residence time of auxiliary 1 be from 0.5 to 360 minutes.

Auxiliary 2 is preferably the aforementioned solvent of the present invention as are preferably used in process stage a).

The esterification of the monohydroxy-functionalized dialkylphosphinic acid (III) or of the monofunctionalized dialkylphosphinic acid (VI) or of the alkylphosphonous acid derivatives (II) and also of the phosphinic acid source (I) to form the corresponding esters can be achieved for example by reaction with higher-boiling alcohols by removing the resultant water by azeotropic distillation, or by reaction with epoxides (alkylene oxides).

Preferably, following step a), the alkylphosphonous acid (II) is directly esterified with an alcohol of the general formula M-OH and/or M'-OH or by reaction with alkylene oxides, as indicated hereinbelow.

M-OH preferably comprises primary, secondary or tertiary alcohols having a carbon chain length of $C_1$-$C_{18}$. Particular preference is given to methanol, ethanol, propanol, isopropanol, n-butanol, 2-butanol, tert-butanol, amyl alcohol and/or hexanol.

M'-OH preferably comprises ethylene glycol, 1,2-propylene glycol, 1,3-propylene glycol, 1,4-butanediol, 2,2-dimethylpropane-1,3-diol, neopentyl glycol, 1,6-hexanediol, 1,4-cyclohexanedimethanol, glycerol, trishydroxymethylethane, trishydroxymethylpropane, pentaerythritol, sorbitol, mannitol, α-naphthol, polyethylene glycols, polypropylene glycols and/or EO-PO block polymers.

Also useful as M-OH and M'-OH are mono- or polyhydric unsaturated alcohols having a carbon chain length of $C_1$-$C_{18}$, for example n-but-2-en-1-ol, 1,4-butenediol and allyl alcohol.

Also useful as M-OH and M'-OH are reaction products of monohydric alcohols with one or more molecules of alkylene oxides, preferably with ethylene oxide and/or 1,2-propylene oxide. Preference is given to 2-methoxyethanol, 2-ethoxyethanol, 2-n-butoxyethanol, 2-(2'-ethylhexyloxy)ethanol, 2-n-dodecoxyethanol, methyl diglycol, ethyl diglycol, isopropyl diglycol, fatty alcohol polyglycol ethers and aryl polyglycol ethers.

M-OH and M'-OH are also preferably reaction products of polyhydric alcohols with one or more molecules of alkylene oxide, more particularly diglycol and triglycol and also adducts of 1 to 6 molecules of ethylene oxide or propylene oxide onto glycerol, trishydroxymethylpropane or pentaerythritol.

Useful M-OH and M'-OH further include reaction products of water with one or more molecules of alkylene oxide. Preference is given to polyethylene glycols and poly-1,2-propylene glycols of various molecular sizes having an average molecular weight of 100-1000 g/mol and more preferably of 150-350 g/mol.

Preference for use as M-OH and M'-OH is also given to reaction products of ethylene oxide with poly-1,2-propylene glycols or fatty alcohol propylene glycols; similarly reaction products of 1,2-propylene oxide with polyethylene glycols or fatty alcohol ethoxylates. Preference is given to such reaction products with an average molecular weight of 100-1000 g/mol, more preferably of 150-450 g/mol.

Also useful as M-OH and M'-OH are reaction products of alkylene oxides with ammonia, primary or secondary amines, hydrogen sulfide, mercaptans, oxygen acids of phosphorus and $C_2$-$C_6$ dicarboxylic acids. Suitable reaction products of ethylene oxide with nitrogen compounds are triethanolamine, methyldiethanolamine, n-butyldiethanolamine, n-dodecyldiethanolamine, dimethylethanolamine, n-butylmethylethanolamine, di-n-butylethanolamine, n-dodecylmethylethanolamine, tetrahydroxyethylethylenediamine or pentahydroxyethyldiethylenetriamine.

Preferred alkylene oxides are ethylene oxide, 1,2-propylene oxide, 1,2-epoxy-butane, 1,2-epoxyethylbenzene, (2,3-epoxypropyl)benzene, 2,3-epoxy-1-propanol and 3,4-epoxy-1-butene.

Suitable solvents are the solvents mentioned in the process step a) and also the M-OH and M'-OH alcohols used and the alkylene oxides. These offer advantages in the form of a higher space-time yield.

The reaction is preferably carried out under the autogenous vapor pressure of the employed alcohol M-OH, M'-OH and alkylene oxide and/or of the solvent.

Preferably, the reaction is carried out at a partial pressure of the employed alcohol M-OH, M'-OH and alkylene oxide of 0.01-100 bar, more preferably at a partial pressure of the alcohol of 0.1-10 bar.

The reaction is preferably carried out at a temperature in the range from −20 to 340° C. and is more preferably carried out at a temperature in the range from 20 to 180° C.

The reaction is preferably carried out at a total pressure in the range from 1 to 100 bar.

The reaction is preferably carried out in a molar ratio for the alcohol or alkylene oxide component to the phosphinic acid source (I) or alkylphosphonous acid (II) or monofunctionalized dialkylphosphinic acid (VI) or monohydroxy-functionalized dialkylphosphinic acid (III) ranging from 10 000:1 to 0.001:1 and more preferably from 1000:1 to 0.01:1.

The reaction is preferably carried out in a molar ratio for the phosphinic acid source (I) or alkylphosphonous acid (II) or monohydroxy-functionalized or monofunctionalized dialkylphosphinic acid (VI) dialkylphosphinic acid (III) to the solvent ranging from 1:10 000 to 1:0 and more preferably in a phosphinic acid/solvent molar ratio ranging from 1:50 to 1:1.

Particularly preferred catalysts B as used in process stage b) are peroxo compounds such as peroxomonosulfuric acid, potassium monopersulfate (potassium peroxomonosulfate), Caroat™, Oxone™, peroxodisulfuric acid, potassium persulfate (potassium peroxodisulfate), sodium persulfate (sodium peroxodisulfate), ammonium persulfate (ammonium peroxodisulfate).

Particularly preferred catalysts B are compounds capable of forming peroxides in the solvent system, such as sodium peroxide, sodium peroxide hydrates, sodium peroxide diperoxohydrate, sodium peroxide diperoxohydrates, lithium peroxide, lithium peroxide hydrates, calcium peroxide, strontium peroxide, barium peroxide, magnesium peroxide, zinc peroxide, potassium hyperoxide, potassium hyperoxide hydrates, sodium peroxoborate, sodium peroxoborate hydrates, potassium peroxoborate peroxohydrate, magnesium peroxoborate, calcium peroxoborate, barium peroxoborate, strontium peroxoborate, potassium peroxoborate, peroxomonophosphoric acid, peroxodiphosphoric acid, potassium peroxodiphosphate, ammonium peroxodiphosphate, potassium ammonium peroxodiphosphates, sodium carbonate peroxohydrate, urea peroxohydrate, ammonium oxalate peroxide, barium peroxide peroxohydrate, barium peroxide peroxohydrate, calcium hydrogen peroxides, calcium peroxide peroxohydrate, ammonium triphosphate diperoxophosphate hydrate, potassium fluoride peroxohydrate, potassium fluoride triperoxohydrate, potassium fluoride diperoxohydrate, sodium pyrophosphate diperoxohydrate, sodium pyrophosphate diperoxohydrate octahydrate, potassium acetate peroxohydrate, sodium phosphate peroxohydrate, sodium silicate peroxohydrate.

Preferred catalysts B are hydrogen peroxide, performic acid, peracetic acid, benzoyl peroxide, di-t-butyl peroxide, dicumyl peroxide, 2,4-dichlorobenzoyl peroxide, decanoyl peroxide, lauryl peroxide, cumene hydroperoxide, pinene hydroperoxide, p-menthane hydroperoxide, t-butyl hydroperoxide, acetylacetone peroxide, methyl ethyl ketone peroxide, succinic acid peroxide, dicetyl peroxydicarbonate, t-butyl peroxyacetate, t-butylperoxymaleic acid, t-butyl peroxybenzoate, acetyl cyclohexylsulfonyl peroxide.

Preferred catalysts B are water-soluble azo compounds. Particular preference is given to azo initiators such as VAZO® 52 2,2'-azobis(2,4-dimethylvaleronitrile), VAZO® 64 (azobis(isobutyronitrile), AIBN), VAZO® 67 2,2'-azobis (2-methyl-butyronitrile), VAZO® 88 1,1'-azobis(cyclohexane-1-carbonitrile), VAZO® 68 from Dupont-Biesteritz, V-70 2,2'-azobis(4-methoxy-2,4-dimethylvaleronitrile), V-65 2,2'-azobis(2,4-dimethylvaleronitrile), V-601 dimethyl 2,2'-azobis(2-methylpropionate), V-59 2,2'-azobis(2-methylbutyronitrile), V-40 1,1'-azobis(cyclohexane-1-carbonitrile), VF-096 2,2'-azobis[N-(2-propenyl)-2-methylpropionamide], V-30 1-[(cyano-1-methylethy)azo]formamide, VAm-110 2,2'-azobis(N-butyl-2-methyl-propionamide), VAm-111 2,2'-azobis(N-cyclohexyl-2-methylpropionamide), VA-046B 2,2'-azobis[2-(2-imidazolin-2-yl)propane disulfate dihydrates, VA-057 2,2'-azobis[N-(2-carboxyethyl)-2-methylpropionamidine] tetrahydrate, VA-061 2,2'-azobis[2-(2-imidazolin-2-yl)propane], VA-080 2,2'-azobis{2-methyl-N-[1,1-bis(hydroxymethyl)-2-hydroxyethyl]propionamide, VA-085 2,2'-azobis{2-methyl-N-[2-(1-hydroxybutyl)]propionamide}, VA-086 2,2'-azobis[2-methyl-N-(2-hydroxyethyl)propionamide] from Wako Chemicals.

It is also possible to use azo initiators such as 2-tert-butylazo-2-cyanopropane, dimethyl azodiisobutyrate, azodiisobutyronitrile, 2-tert-butylazo-1-cyano-cyclohexane, 1-tert-amylazo-1-cyanocyclohexane. Preference is further given to alkyl perketals such as 2,2-bis-(tert-butylperoxy) butane, ethyl 3,3-bis(tert-butyl-peroxy)butyrate, 1,1-di(tert-butylperoxy)cyclohexane.

Preferred catalysts B are also metals, metal hydrides and metal alkoxides such as, for example, lithium, lithium hydride, lithium aluminohydride, methyllithium, butyllithium, tert-butyllithium, lithium diisopropylamide, sodium, sodium hydride, sodium borohydride, sodium methoxide, sodium ethoxide, sodium butoxide, potassium methoxide, potassium ethoxide or potassium butoxide.

The catalyst B is preferably used in amounts of 0.05 to 5 mol % based on the respective acroleins (V).

The catalyst B is preferably used in amounts of 0.001 to 10 mol %, based on the phosphorus-containing compound.

The catalyst B is preferably metered in at a rate of 0.01 to 10 mol % of catalyst per hour, based on the phosphorus-containing compound.

Suitable solvents are those used above in process stage a).

The reaction of the alkylphosphonous acids (II) with acrolein (V) is preferably carried out at a temperature of 0 to 250° C., more preferably at 20 to 200° C. and more particularly at 50 to 150° C.

The atmosphere for the reaction with acrolein (V) preferably consists of constituents of the solvent and acrolein (V) to an extent of 50% to 99.9% by weight, preferably 70-95%.

The reaction during the addition of acrolein (V) is preferably carried out at a pressure of 1-20 bar.

In a further embodiment of the method, the product mixture obtained after process stage a) and/or b) is worked up.

In a further embodiment of the method, the product mixture obtained after process stage a) is worked up and thereafter the monofunctionalized dialkylphosphinic acids and/or their esters and alkali metal salts obtained after process stage b) are reacted in process stage c).

The invention further provides a method in step b) for continuous production of monofunctionalized dialkylphosphinic esters (VI) by reaction of alkylphosphonous esters (II) with acrolein (V) in the presence of metal alkoxides (catalyst B), which method comprises
a) initially charging a self-contained reactor configured to circulate the reaction mixture and equipped with cooling means and also an overflow with a volume corresponding to the reactor volume of the monofunctionalized dialkylphosphinic esters (VI) to be produced, optionally mixed with the alcohol corresponding to the metal alkoxide as solvent, and recirculating,
b) the alkylphosphonous ester (II), the acrolein (V) and also an alcoholic solution of the metal alkoxide being continuously introduced into the reactor with cooling of the recirculated reactor contents, and reacted at a temperature of about 0 to 80° C. in the course of about 5-120 minutes, wherein the molar ratio of the alkylphosphonous ester (II) to the acrolein (V) is about 1:0.9-2 and the amount of the metal alkoxide, based on the alkylphosphonous ester (II), is about 0.1 to 5 mol %; and
c) continuously withdrawing, over the overflow of the reactor, a mixture comprising the process product and separating the monofunctionalized dialkyl-phosphinic ester (VI) from the mixture by distillation.

In a preferred embodiment of the method according to the present invention, the reaction of the reaction components is carried out at a temperature of 20 to 50° C.

The charging of the reactor with the reaction components and the catalyst solution can be carried out for example by a) passing the alkylphosphonous ester (II), the acrolein (V) and also the alcoholic solution of the metal alkoxide into the reactor separately,
b) passing a mixture of the alkylphosphonous ester (II) with the acrolein (V) into the reactor separately from the alcoholic solution of the metal alkoxide, or
c) passing a mixture of the alkylphosphonous ester (II) with the alcoholic solution of the metal alkoxide into the reactor separately from the acrolein (V).

It is further advantageous when the alcohol used as solvent and/or the alcoholic component of the metal alkoxide correspond to the alcoholic component of the alkylphosphonous ester (II).

When alkylphosphonous ester (II) and the alcoholic metal alkoxide solution are used with different alcoholic components, a mixed product will be obtained as process product.

Lastly, preferred features of the invention consist in the molar ratio of alkylphosphonous ester (II) to acrolein (V) being in the range from 1:1-1.3, the amount of catalyst B based on the alkylphosphonous ester (II) being 1-5 mol % and the amount of the alcohol used as solvent being 0.1-1000 mol per mole of alkylphosphonous ester (II).

The method of the present invention makes it possible to produce monofunctionalized dialkylphosphinic ester (VI) continuously on an industrial scale in a hitherto unattained yield of about 90% of theory.

The reaction described in step c) is achieved by hydrogenation of the monofunctionalized dialkylphosphinic acid, its salts and esters (VI) via selective hydrogenation by means of a reducing agent or catalytically by means of hydrogen in the presence of a catalyst C and optionally of an amine and of a promoter.

Preferred reducing agents are represented by metal hydrides, boron hydrides, metal borohydrides, aluminum hydrides, metal aluminohydrides. Examples of preferred reducing agents are decaborane, diborane, diisobutylaluminum hydride, dimethyl sulfide borane, dimethyl sulfide borane, copper hydride, lithium aluminohydride, sodium bis(2-methoxyethoxy)aluminohydride, sodium borohydride, sodium triacetoxyborohydride, nickel borohydride, tributyltin hydride, tin hydride.

The reaction is preferably carried out in a dialkylphosphinic acid/reducing agent molar ratio in the range from 1:10 to 1:0.1 and more preferably in a dialkylphosphinic acid/reducing agent molar ratio in the range from 1:2 to 1:0.25.

The preferred catalytic hydrogenation is effected by means of hydrogen in the presence of a catalyst C and optionally of an amine and/or of a promoter.

The catalyst C as used for process step c) for the reaction of the mono-functionalized dialkylphosphinic acid derivative VI with hydrogen and, where appropriate, a promoter to form the monoamino-functionalized dialkylphosphinic acid derivative (III) may preferably be the catalyst A.

Diphenyl p-, m- or o-tolyl phosphite, di-p-, -m- or -o-tolyl phenyl phosphite, m-tolyl o-tolyl p-tolyl phosphite, o-tolyl p- or m-tolyl phenyl phosphite, di-p-tolyl m- or o-tolyl phosphite, di-m-tolyl p- or o-tolyl phosphite, tri-m-, -p- or -o-tolyl phosphite, di-o-tolyl m- or p-tolyl phosphite; tris(2-ethylhexyl)phosphite, tribenzyl phosphite, trilauryl phosphite, tri-n-butyl phosphite, triethyl phosphite, tri-neopentyl phosphite, tri-i-propyl phosphite, tris(2,4-di-t-butylphenyl) phosphite, tris(2,4-di-tert-butyl-phenyl)phosphite, diethyl trimethylsilyl phosphite, diisodecyl phenyl phosphite, dimethyl trimethylsilyl phosphite, triisodecyl phosphite, tris(tert-butyldimethylsilyl)phosphite, tris(2-chloroethyl phosphite, tris(1,1,1,3,3,3-hexafluoro-2-propyl)phosphite, tris(nonylphenyl)phosphite, tris(2,2,2-trifluoroethyl)phosphite, tris (trimethylsilyl)phosphite, 2,2-dimethyltrimethylene phenyl phosphite, trioctadecyl phosphite, triimethylolpropane phosphite, benzyldiethyl phosphite, (R)-binaphthyl isobutyl phosphite, (R)-binaphthyl cyclopentyl phosphite, (R)-binaphthyl isopropyl phosphite, tris(2-tolyl)phosphite, tris(nonylphenyl)phosphite, methyl diphenyl phosphite; (11aR)-(+)-10,11,12,13-tetra-hydrodiindeno[7,1-de:1',7'-fg][1,3,2]dioxaaphosphocine-5-phenoxy, 4-ethyl-2,6,7-trioxa-1-phosphabicyclo[2.2.2]octane, (11bR,11'bR)-4,4'-(9,9-dimethyl-9H-xanthene-4,5-diyl)bisdinaphtho[2,1-d:1',2'-f][1,3,2]dioxaphosphepine, (11bR,11'bR)-4,4'-(oxydi-2,1-phenylene)bisdinaphtho[2,1-d:,1',2'-f][1,3,2]dioxaphosphepine, (11bS,11'bS)-4,4'-(9,9-dimethyl-9H-xanthene-4,5-diyl)bis-dinaphtho[2,1-d:1',2'-f][1,3,2]dioxaphosphepine, (11bS,11'bS)-4,4'-(oxydi-2,1-phenylene) bisdinaphtho[2,1-d:1',2'-f][1,3,2]dioxaphosphepine, 1,1'-bis[(11bR)- and 1,1'-bis[(11bS)-dinaphtho[2,1-d:1',2'-f][1,3,2] dioxaphosphepine-4-yl]ferrocene; dimethyl phenylphosphonite, diethyl methylphosphonite, diethyl phenylphosphonite, diisopropyl phenylphosphonite; methyl methylphenylphosphinite, isopropyl isopropylphenylphosphinite, ethyl diphenylphosphinite and methyl diphenylphosphinite.

In addition to the bidentate ligands listed under catalyst A, the following compounds can also be used:

1,2-bis(diadamantylphosphinomethyl)benzene, 1,2-bis(di-3,5-dimethyladamantyl-phosphinomethyl)benzene, 1,2-bis(di-5-tert-butyladamantaylphosphino-methyl)benzene, 1,2-bis(1-adamantyl tert-butylphosphinomethyl)benzene, 1-(di-tert-butylphosphinomethyl)benzene, 1-(diadamantylphosphinomethyl)-2-(phosphaadamantylphosphinomethyl)benzene, 1,2-bis(di-tert-butylphosphino-methyl)ferrocene, 1,2-bis(dicyclohexylphosphinomethyl)ferrocene, 1,2-bis(di-isobutylphosphinomethyl)ferrocene, 1,2-bis(dicyclopentylphosphino-methyl)ferrocene, 1,2-bis(diethylphosphinomethyl)ferrocene, 1,2-bis(diisopropyl-phosphinomethyl)ferrocene, 1,2-bis(dimethylphosphinomethyl) ferrocene, 9,9-dimethyl-4,5-bis(diphenoxyphosphine) xanthene, 9,9-dimethyl-4,5-bis(di-p-methylphenoxyphosphine)xanthene, 9,9-dimethyl-4,5-bis (di-o-methylphenoxy-phosphine)xanthene, 9,9-dimethyl-4,5-bis(di-1,3,5-trimethylphenoxyphos-phine)xanthene, 9,9-dimethyl-4,5-bis(diphenoxyphosphine)-2,7-di-tert-butylxanthene, 9,9-dimethyl-4,5-bis(di-o-methylphenoxyphosphine)-2,7-di-tert-butylxanthene, 9,9-dimethyl-4,5-bis(di-p-methylphenoxyphosphine)-2,7-di-tert-butylxanthene, 9,9-dimethyl-4,5-bis(di-1,3,5-trimethylphenoxyphosphine)-2,7-di-tert-butylxanthene, 1,1'-bis(diphenoxyphosphine)ferrocene, 1,1'-bis(di-o-methylphenoxy)ferrocene, 1,1'-bis(di-p-methylphenoxyphosphine)ferrocene, 1,1'-bis(di-1,3,5-trimethylphenoxyphosphine)ferrocene, 2,2'-bis(diphenoxyphosphine)-1,1'-binaphthyl, 2,2'-bis(di-o-methylphenoxyphosphine)-1,1'-binaphthyl, 2,2'-bis(di-p-methylphenoxyphosphine)-1,1'-binaphthyl, 2,2'-bis(di-1,3,5-trimethylphenoxyphosphine)-1,1-binaphthyl, (oxydi-2,1-phenylene)bis(diphenoxyphosphine), (oxydi-2,1-phenylene)bis(di-o-methylphenoxyphosphine), (oxydi-2,1-phenylene)bis(di-p-methylphenoxyphosphine), (oxydi-2,1-phenylene)bis(di-1,3,5-trimethylphenoxyphosphine), 2,2'-bis (diphenoxyphosphine)-1,1'-biphenyl, 2,2'-bis(di-o-methylphenoxyphosphine)-1,1'-biphenyl, 2,2'-bis(di-p-methylphenoxyphos-phine)-1,1'-biphenyl, 2,2'-bis(di-1,3,5-trimethylphenoxyphosphine)-1,1'-biphenyl, 1,2-bis(di-(1,3,5,7-tetramethyl-6,9,10-trioxa-2-phosphaadamantylmethyl) ferrocene, 1-(tert-butoxycarbonyl)-(2S,4S)-2-[(diphenylphosphino)methyl]-4-(dibenzophospholyl) pyrrolidine, 1-(tert-butoxycarbonyl)-(2S,4S)-2-[(dibenzophospholyOmethyl]-4-(diphenylphosphino) pyrrolidine, 1-(tert-butoxycarbonyl)-(2S,4S)-4-(dibenzophospholyl)-2-[(dibenzophospholyl)methyl]-pyrrolidine, BINAPHOS, kelliphite, chiraphite, bis-3,4-diazophospholane; bis(phospholane) ligands, such as bis(2,5-trans-dialkylphospholane), bis(2,4-trans-dialkylphosphethane), 1,2-bis(phenoxyphosphine)ethane, 1,2-bis(3-methylphenoxyphosphine)ethane, 1,2-bis(2-methylphenoxyphosphine)ethane, 1,2-bis(1-methylphenoxyphosphine)ethane, 1,2-bis(1,3,5-trimethylphenoxy-phosphine)ethan, 1,3-bis(phenoxyphosphine)propane, 1,3-bis(3-methylphenoxyphosphine)propane, 1,3-bis(2-methylphenoxyphosphine)propane, 1,3-bis(1-methylphenoxyphosphine)propane, 1,3-bis(1,3,5-trimethylphenoxyphos-phine)propane, 1,4-bis (phenoxyphosphine)butane, 1,4-bis(3-methylphenoxyphosphine)butane, 1,4-bis(2-methylphenoxyphosphine)butane, 1,4-bis(1-methyl-phenoxyphosphine)butane, 1,4-bis(1,3,5-trimethylphenoxyphosphine)butane.

The proportion of catalyst C based on the monofunctionalized dialkyiphosphinic acid (VI) used is preferably in the range from 0.00001 to 20 mol % and more preferably in the range from 0.00001 to 10 mol %.

The hydrogenation reaction preferably takes place in the presence of an amine.

Preferred amines are ammonia, monoamines, diamines, higher amines.

Preferred monoamines are for example amines of the formula $R^1$—$NH_2$, where R' is linear or branched $C_{1-20}$-alkyl. Preference is given to methylamine, ethylamine, propylamine, i-propylamine, butylamine, i-butylamine, pentylamine and 2-ethylhexylamine.

Preferred diamines are for example amines of the formula $R^1$—$NH_2$, where R' is linear or branched $C_{1-20}$-alkyl. Preference is given to ethylenediamine, propylenediamine, diaminobutane, pentamethylenediamine and hexamethylenediamine.

When ammonia is used as amine, the partial pressure of the ammonia is preferably in the range from 0.01 to 100 bar, more preferably in the range from 0.05 to 50 bar and more particularly in the range from 0.1 to 20 bar.

The concentration of ammonia in the reaction mixture is preferably in the range from 1% to 30% by weight and more preferably in the range from 5% to 25% by weight.

The concentration of monoamine and/or diamine in the reaction mixture is preferably in the range from 1% to 80% by weight and more preferably in the range from 5% to 60% by weight.

The hydrogenation reaction is preferably carried out in the presence of a promoter, preferred promoters being alkali metal and alkaline earth metal hydroxides and alkoxides. Examples of preferred promoters are NaOH, KOH, $Mg(OH)_2$, $Ca(OH)_2$, $Ba(OH)_2$ and also sodium methoxide, potassium methoxide, sodium ethoxide or sodium butoxide, of which NaOH and KOH are particularly preferred.

The ratio of promoter to catalyst is preferably about 0.001:1 to 0.5:1, more preferably about 0.01:1 to 0.2:1 and even more preferably 0.04:1 to 0.1:1.

It is preferable to add initially at least a portion of the promoter and secondly the amine to the catalyst and/or the solution/suspension which the catalyst contains. It is preferable to add initially at least 10% by weight, preferably 20% by weight and more preferably 50% by weight of the promoter.

It is particularly preferable to add 100% by weight of the promoter.

It is particularly preferable to use the transition metals in their zerovalent state.

The catalyst having a heterogeneous action is preferably active during the reaction as a suspension or bound to a solid phase.

The reaction preferably takes place in a solvent as a single-phase system in homogeneous or heterogeneous mixture and/or in the gas phase.

Suitable solvents are those used above in process stage a).

The reaction is preferably carried out in a dialkylphosphinic acid/solvent molar ratio of 1:10 000 to 1:0 and more preferably in a dialkylphosphinic acid/solvent molar ratio of 1:50 to 1:1.

The reaction temperature is preferably in the range from 20 to 200° C. and more preferably in the range from 40 to 150° C. and more particularly from 60 to 100° C.

The reaction time is preferably in the range from 0.1 to 20 hours.

The reaction is preferably carried out under the partial pressure of the hydrogen and/or of the solvent.

The process step of the method of the present invention is preferably carried out at a hydrogen partial pressure of 0.1 to 100 bar, more preferably at 0.5 to 50 bar and more particularly at 1 to 20 bar.

The process step of the method of the present invention is preferably carried out at an absolute pressure of from 0.1 to 150 bar, more preferably 0.5 to 70 bar and more particularly 1 to 30 bar.

The hydrogenation of the present invention can be carried out in liquid phase, in the gas phase or else in supercritical phase. In this case the catalyst is used in the case of liquid, preferably in homogeneous form or as a suspension, while a fixed bed arrangement is of advantage in the case of gas phase or supercritical operation.

The monohydroxy-functionalized dialkylphosphinic acid or salt (III) can thereafter be converted into further metal salts.

The metal compounds which are used in process stage d) preferably comprise compounds of the metals Mg, Ca, Al, Sb, Sn, Ge, Ti, Fe, Zr, Zn, Ce, Bi, Sr, Mn, Li, Na, K, more preferably Mg, Ca, Al, Ti, Zn, Sn, Ce, Fe.

Suitable solvents for process stage d) are those used above in process stage a).

The reaction of process stage d) is preferably carried out in an aqueous medium.

Process stage d) preferably comprises reacting the monohydroxy-functionalized dialkylphosphinic acids, esters and/or alkali metal salts (III) obtained after process stage c) with metal compounds of Mg, Ca, Al, Zn, Ti, Sn, Zr, Ce or Fe to form the monohydroxy-functionalized dialkylphosphinic acid salts (III) of these metals.

The reaction is carried out in a molar ratio of monohydroxy-functionalized dialkylphosphinic acid, ester or salt (III) to metal in the range from 8:1 to 1:3 (for tetravalent metal ions or metals having a stable tetravalent oxidation state), from 6:1 to 1:3 (for trivalent metal ions or metals having a stable trivalent oxidation state), from 4:1 to 1:3 (for divalent metal ions or metals having a stable divalent oxidation state) and from 3:1 to 1:4 (for monovalent metal ions or metals having a stable monovalent oxidation state).

Preferably, monohydroxy-functionalized dialkylphosphinic acid, ester or salt (III) obtained in process stage c) is converted into the corresponding dialkylphosphinic acid and the latter is reacted in process stage d) with metal compounds of Mg, Ca, Al, Zn, Ti, Sn, Zr, Ce or Fe to form the monohydroxy-functionalized dialkylphosphinic acid salts (III) of these metals.

Preferably, monohydroxy-functionalized dialkylphosphinic acid/ester (III) obtained in process stage c) is converted to a dialkylphosphinic acid alkali metal salt and the latter is reacted in process stage d) with metal compounds of Mg, Ca, Al, Zn, Ti, Sn, Zr, Ce or Fe to form the monohydroxy-functionalized dialkylphosphinic acid salts (III) of these metals.

The metal compounds of Mg, Ca, Al, Zn, Ti, Sn, Zr, Ce or Fe for process stage d) preferably comprise metals, metal oxides, hydroxides, oxide hydroxides, borates, carbonates, hydroxocarbonates, hydroxocarbonate hydrates, mixed metal hydroxocarbonates, mixed metal hydroxocarbonate hydrates, phosphates, sulfates, sulfate hydrates, hydroxosulfate hydrates, mixed metal hydroxosulfate hydrates, oxysulfates, acetates, nitrates, fluorides, fluoride hydrates, chlorides, chloride hydrates, oxychlorides, bromides, iodides, iodide hydrates, carboxylic acid derivatives and/or alkoxides.

The metal compounds preferably comprise aluminum chloride, aluminum hydroxide, aluminum nitrate, aluminum sulfate, titanyl sulfate, zinc nitrate, zinc oxide, zinc hydroxide and/or zinc sulfate.

Also suitable are aluminum metal, fluoride, hydroxychloride, bromide, iodide, sulfide, selenide; phosphide, hypophosphite, antimonide, nitride; carbide, hexafluorosilicate; hydride, calcium hydride, borohydride; chlorate; sodium aluminum sulfate, aluminum potassium sulfate, aluminum ammonium sulfate, nitrate, metaphosphate, phosphate, silicate, magnesium silicate, carbonate, hydrotalcite, sodium carbonate, borate, thiocyanate oxide, oxide hydroxide, their corresponding hydrates and/or polyaluminum hydroxy compounds, which preferably have an aluminum content of 9 to 40% by weight.

Also suitable are aluminum salts of mono-, di-, oligo-, polycarboxylic acids such as, for example, aluminum diacetate, acetotartrate, formate, lactate, oxalate, tartrate, oleate, palmitate, stearate, trifluoromethanesulfonate, benzoate, salicylate, 8-oxyquinolate.

Likewise suitable are elemental, metallic zinc and also zinc salts such as for example zinc halides (zinc fluoride, zinc chlorides, zinc bromide, zinc iodide).

Also suitable are zinc borate, carbonate, hydroxide carbonate, silicate, hexafluorosilicate, stannate, hydroxide stannate, magnesium aluminum hydroxide carbonate; nitrate, nitrite, phosphate, pyrophosphate; sulfate, phosphide, selenide, telluride and zinc salts of the oxoacids of the seventh main group (hypohalites, halites, halates, for example zinc iodate, perhalates, for example zinc perchlorate); zinc salts of the pseudohalides (zinc thiocyanate, zinc cyanate, zinc cyanide); zinc oxides, peroxides, hydroxides or mixed zinc oxide hydroxides.

Preference is given to zinc salts of the oxoacids of transition metals (for example zinc chromate(VI) hydroxide, chromite, molybdate, permanganate, molybdate).

Also suitable are zinc salts of mono-, di-, oligo-, polycarboxylic acids, for example zinc formate, acetate, trifluoroacetate, propionate, butyrate, valerate, caprylate, oleate, stearate, oxalate, tartrate, citrate, benzoate, salicylate, lactate, acrylate, maleate, succinate, salts of amino acids (glycine), of acidic hydroxyl functions (zinc phenoxide etc), zinc p-phenolsulfonate, acetylacetonate, stannate, dimethyldithiocarbamate, trifluoromethanesulfonate.

In the case of titanium compounds, metallic titanium is as is titanium(III) and/or (IV) chloride, nitrate, sulfate, formate, acetate, bromide, fluoride, oxychloride, oxysulfate, oxide, n-propoxide, n-butoxide, isopropoxide, ethoxide, 2-ethylhexyl oxide.

Also suitable is metallic tin and also tin salts (tin(II) and/or (IV) chloride); tin oxides and tin alkoxide such as, for example, tin(IV) tert-butoxide.

Cerium(III) fluoride, chloride and nitrate are also suitable.

In the case of zirconium compounds, metallic zirconium is preferred as are zirconium salts such as zirconium chloride, zirconium sulfate, zirconyl acetate, zirconyl chloride. Zirconium oxides and also zirconium (IV) tert-butoxide are also preferred.

The reaction in process stage d) is preferably carried out at a solids content of the monohydroxy-functionalized dialkylphosphinic acid salts in the range from 0.1% to 70% by weight, preferably 5% to 40% by weight.

The reaction in process stage d) is preferably carried out at a temperature of 20 to 250° C., preferably at a temperature of 80 to 120° C.

The reaction in process stage d) is preferably carried out at a pressure between 0.01 and 1000 bar, preferably 0.1 to 100 bar.

The reaction in process stage d) preferably takes place during a reaction time in the range from $1*10^{-7}$ to $1*10^2$ h.

Preferably, the monohydroxy-functionalized dialkylphosphinic acid salt (III) removed after process stage d) from the reaction mixture by filtration and/or centrifugation is dried.

Preferably, the product mixture obtained after process stage c) is reacted with the metal compounds without further purification.

Preferred solvents are the solvents mentioned in process step a).

The reaction in process stage d), c) and/or b) is preferably carried out in the solvent system given by stage a).

The reaction in process stage d) is preferred in a modified given solvent system. Acidic components, solubilizers, foam inhibitors, etc are added for this pupose.

In a further embodiment of the method, the product mixture obtained after process stage a), b) and/or c) is worked up.

In a further embodiment of the method, the product mixture obtained after process stage c) is worked up and thereafter the monohydroxy-functionalized dialkylphosphinic acids and/or salts or esters (III) obtained after process stage c) are reacted in process stage d) with the metal compounds.

Preferably, the product mixture after process stage c) is worked up by isolating the monohydroxy-functionalized dialkylphosphinic acids and/or salts or esters (III) by removing the solvent system, for example by evaporation.

Preferably, the monohydroxy-functionalized dialkylphosphinic acid salt (III) of the metals Mg, Ca, Al, Zn, Ti, Sn, Zr, Ce or Fe selectively has a residual moisture content of 0.01% to 10% by weight, preferably of 0.1% to 1% by weight, an average particle size of 0.1 to 2000 μm, preferably of 10 to 500 μm, a bulk density of 80 to 800 g/l, preferably 200 to 700 g/l, and a Pfrengle flowability of 0.5 to 10, preferably of 1 to 5.

The molded articles, films, threads and fibers more preferably contain from 5% to 30% by weight of the monohydroxy-functionalized dialkylphosphinic acid/ester/salts produced according to one or more of claims 1 to 11, from 5% to 90% by weight of polymer or mixtures thereof, from 5% to 40% by weight of additives and from 5% to 40% by weight of filler, wherein the sum total of the components is always 100% by weight.

The additives preferably comprise antioxidants, antistats, blowing agents, further flame retardants, heat stabilizers, impact modifiers, processing aids, lubricants, light stabilizers, antidripping agents, compatibilizers, reinforcing agents, fillers, nucleus-forming agents, nucleating agents, additives for laser marking, hydrolysis stabilizers, chain extenders, color pigments, softeners, plasticizers and/or plasticizing agents.

Preference is given to a flame retardant containing 0.1 to 90% by weight of the halogen-depleted monohydroxy-functionalized dialkylphosphinic acid, ester and salts (III) and 0.1% to 50% by weight of further additives, more preferably diols.

Preferred additives are also aluminum trihydrate, antimony oxide, brominated aromatic or cycloaliphatic hydrocarbons, phenols, ethers, chloroparaffin, hexachlorocyclopentadiene adducts, red phosphorus, melamine derivatives, melamine cyanurates, ammonium polyphosphates and magnesium hydroxide. Preferred additives are also further flame retardants, more particularly salts of dialkylphosphinic acids.

More particularly, the present invention provides for the use of the present invention monohydroxy-functionalized dialkylphosphinic acid, esters and salts (III) as flame retardants or as an intermediate in the manufacture of flame retardants for thermoplastic polymers such as polyesters, polystyrene or polyamide and for thermoset polymers such as unsaturated polyester resins, epoxy resins, polyurethanes or acrylates.

Suitable polyesters are derived from dicarboxylic acids and their esters and diols and/or from hydroxycarboxylic acids or the corresponding lactones.

It is preferable to use terephthalic acid and ethylene glycol, 1,3-propanediol and 1,3-butanediol.

Suitable polyesters include inter alia polyethylene terephthalate, polybutylene terephthalate (Celanex® 2500, Celanex® 2002, from Celanese; Ultradur®, from BASF), poly-1,4-dimethylolcyclohexane terephthalate, polyhydroxybenzoates, and also block polyether esters derived from polyethers having hydroxyl end groups; and also polyesters modified with polycarbonates or MBS.

Synthetic linear polyesters having permanent flame retardancy are composed of dicarboxylic acid components, diol components of the present invention monohydroxy-functionalized dialkylphosphinic acids and ester, or of the monohydroxy-functionalized dialkylphosphinic acids and esters produced by the method of the present invention as phosphorus-containing chain members. The phosphorus-containing chain members account for 2-20% by weight of the dicarboxylic acid component of the polyester. The resulting phosphorus content in the polymer is preferably 0.1-5% by weight, more preferably 0.5-3% by weight.

The following steps can be carried out with or by addition of the compounds produced according to the present invention.

Preferably, the molding material is produced from the free dicarboxylic acid and diols by initially esterifying directly and then polycondensing.

When proceeding from dicarboxylic esters, more particularly dimethyl esters, it is preferable to first transesterify and then to polycondense by using catalysts customary for this purpose.

Polyester production may preferably proceed by adding customary additives (crosslinking agents, matting agents and stabilizing agents, nucleating agents, dyes and fillers, etc) in addition to the customary catalysts.

The esterification and/or transesterification involved in polyester production is preferably carried out at temperatures of 100-300° C., more preferably at 150-250° C.

The polycondensation involved in polyester production preferably takes place at pressures between 0.1 to 1.5 mbar and temperatures of 150-450° C., more preferably at 200-300° C.

The flame-retardant polyester molding materials produced according to the present invention are preferably used in polyester molded articles.

Preferred polyester molded articles are threads, fibers, self-supporting films/sheets and molded articles containing mainly terephthalic acid as dicarboxylic acid component and mainly ethylene glycol as diol component.

The resulting phosphorus content in threads and fibers produced from flame-retardant polyesters is preferably 0.1%-18%, more preferably 0.5%-15% by weight and in the case of self-supporting films/sheets 0.2%-15%, preferably 0.9%-12% by weight.

Suitable polystyrenes are polystyrene, poly(p-methylstyrene) and/or poly(alpha-methylstyrene).

Suitable polystyrenes preferably comprise copolymers of styrene or alpha-methylstyrene with dienes or acrylic derivatives, for example styrene-butadiene, styrene-acrylonitrile, styrene-alkyl methacrylate, styrene-butadiene-alkyl acrylate and styrene-butadiene-alkyl methacrylate, styrene-maleic anhydride, styrene-acrylonitrile-methyl acrylate; mixtures of high impact strength from styrene copolymers and another polymer, for example a polyacrylate, a diene polymer or an ethylene-propylene-diene terpolymer; also block copolymers of styrene, for example styrene-butadiene-styrene, styrene-isoprene-styrene, styrene-ethylene/butylene-styrene or styrene-ethylene/propylene-styrene.

Suitable polystyrenes preferably also comprise graft copolymers of styrene or alpha-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on poly(alkyl acrylate)s or poly(alkyl methacrylate)s, styrene and acrylonitrile on acrylate-butadiene copolymers, and also their mixtures, as are also known for example as ABS, MBS, ASA or AES polymers.

The polymers preferably comprise polyamides and copolyamides derived from diamines and dicarboxylic acids and/or from amino carboxylic acids or the corresponding lactams, such as nylon-2,12, nylon-4, nylon-4,6, nylon-6, nylon-6,6, nylon-6,9, nylon-6,10, nylon-6,12, nylon-6,66, nylon-7,7, nylon-8,8, nylon-9,9, nylon-10,9, nylon-10,10, nylon-11, nylon-12, and so on. Such polyamides are known for example under the trade names Nylon®, from DuPont, Ultramid®, from BASF, Akulon® K122, from DSM, Zytel® 7301, from DuPont; Durethan® B 29, from Bayer and Grillamid®, from Ems Chemie.

Also suitable are aromatic polyamides proceeding from m-xylene, diamine and adipic acid; polyamides produced from hexamethylenediamine and iso- and/or terephthalic acid and optionally an elastomer as modifier, for example poly-2,4,4-trimethylhexamethyleneterephthalamide or poly-m-phenyleneisophthalamide, block copolymers of the aforementioned polyamides with polyolefins, olefin copolymers, ionomers or chemically bonded or grafted elastomers or with polyethers, for example with polyethylene glycol, polypropylene glycol or polytetramethylene glycol. Also EPDM- or ABS-modified polyamides or copolyamides; and also polyamides condensed during processing ("RIM polyamide systems").

The monohydroxy-functionalized dialkylphosphinic acid/ester/salts produced according to one or more of claims 1 to 11 are preferably used in molding materials further used for producing polymeric molded articles.

It is particularly preferable for the flame-retardant molding material to contain from 5% to 30% by weight of monohydroxy-functionalized dialkylphosphinic acids, salts or esters produced according to one or more of claims 1 to 11, from 5% to 90% by weight of polymer or mixtures thereof, from 5% to 40% by weight of additives and 5% to 40% by weight of filler, wherein the sum total of the components is always 100% by weight.

The present invention also provides flame retardants containing monohydroxy-functionalized dialkylphosphinic acids, salts or esters produced according to one or more of claims 1 to 11.

The present invention also provides polymeric molding materials and also polymeric molded articles, films, threads and fibers containing the monohydroxy-functionalized dialkylphosphinic acid salts (III) of the metals Mg, Ca, Al, Zn, Ti, Sn, Zr, Ce or Fe produced according to the present invention.

The examples which follow illustrate the invention.

Production, processing and testing of flame-retardant polymeric molding materials and flame-retardant polymeric molded articles.

The flame-retardant components are mixed with the polymeric pellets and any additives and incorporated on a twin-screw extruder (Leistritz LSM® 30/34) at temperatures of 230 to 260° C. (glassfiber-reinforced PBT) or of 260 to 280° C. (glassfiber-reinforced PA 66). The homogenized polymeric strand was hauled off, water bath cooled and then pelletized.

After sufficient drying, the molding materials were processed on an injection molding machine (Aarburg Allrounder) at melt temperatures of 240 to 270° C. (glassfiber-reinforced PBT) or of 260 to 290° C. (glassfiber-reiforced PA 66) to give test specimens. The test specimens are subsequently flammability tested and classified using the UL 94 (Underwriter Laboratories) test.

UL 94 (Underwriter Laboratories) fire classification was determined on test specimens from each mixture, using test specimens 1.5 mm in thickness.

The UL 94 fire classifications are as follows:

V-0: Afterflame time never longer than 10 sec, total of afterflame times for 10 flame applications not more than 50 sec, no flaming drops, no complete consumption of the specimen, afterglow time for specimens never longer than 30 sec after end of flame application.

V-1: Afterflame time never longer than 30 sec after end of flame application, total of afterflame time for 10 flame applications not more than 250 sec, afterglow time for specimens never longer than 60 sec after end of flame application, other criteria as for V-0

V-2: Cotton indicator ignited by flaming drops, other criteria as for V-1 Not classifiable (ncl): does not comply with fire classification V-2.

Some investigated specimens were also tested for their LOI value. The LOI (Limiting Oxygen Index) value is determined according to ISO 4589. According to ISO 4589, the LOI is the lowest oxygen concentration in volume percent which in a mixture of oxygen and nitrogen will support combustion of the plastic. The higher the LOI value, the greater the flammability resistance of the material tested.

| | | |
|---|---|---|
| LOI | 23 | flammable |
| LOI | 24-28 | potentially flammable |
| LOI | 29-35 | flame resistant |
| LOI | >36 | particularly flame-resistant |

Chemicals and Abbreviations Used
VE water completely ion-free water
AIBN azobis(isobutyronitrile), (from WAKO Chemicals GmbH)
WakoV65 2,2'-azobis(2,4-dimethylvaleronitrile), (from WAKO Chemicals GmbH)
Deloxan® THP II metal scavenger (from Evonik Industries AG)

EXAMPLE 1

At room temperature, a three-neck flask equipped with stirrer and high-performance condenser is initially charged with 188 g of water and this initial charge is devolatilized by stirring and passing nitrogen through it. Then, under nitrogen, 0.2 mg of palladium(II) sulfate and 2.3 mg of tris(3-sulfophenyl)phosphine trisodium salt are added, the mixture is stirred, and then 66 g of phosphinic acid in 66 g of water are added. The reaction solution is transferred to a 2 l Büchi reactor and charged with ethylene under superatmospheric pressure while stirring and the reaction mixture is heated to 80° C. After 28 g of ethylene has been taken up, the system is cooled down and free ethylene is discharged. The reaction mixture is freed of solvent on a rotary evaporator. The residue is admixed with 100 g of VE water and at room temperature stirred under nitrogen, then filtered and the filtrate is extracted with toluene, thereafter freed of solvent on a rotary evaporator and the resulting ethylphosphonous acid is collected. Yield: 92 g (98% of theory) of ethylphosphonous acid.

EXAMPLE 2

Example 1 is repeated with 99 g of phosphinic acid, 396 g of butanol, 42 g of ethylene, 6.9 mg of tris(dibenzylideneacetone)dipalladium, 9.5 mg of 4,5-bis(diphenylphosphino)-9,9-dimethylxanthene, followed by purification over a column charged with Deloxan® THP II and the further addition of n-butanol. At a reaction temperature of 80-110° C., the water formed is removed by azeotropic distillation. The product is purified by distillation at reduced pressure. Yield: 189 g (84% of theory) of butyl ethylphosphonite.

EXAMPLE 3

Example 1 is repeated with 198 g of phosphinic acid, 198 g of water, 84 g of ethylene, 6.1 mg of palladium(II) sulfate, 25.8 mg of 9,9-dimethyl-4,5-bis(diphenylphosphino)-2,7-sulfonatoxanthene disodium salt, followed by purification over a column charged with Deloxan® THP II and the further addition of n-butanol. At a reaction temperature of 80-110° C., the water formed is removed by azeotropic distillation. The product is purified by distillation at reduced pressure. Yield: 374 g (83% of theory) of butyl ethylphosphonite.

EXAMPLE 4

A 500 ml five-neck flask equipped with gas inlet tube, thermometer, high-performance stirrer and reflux condenser with gas incineration is charged with 94 g (1 mol) of ethylphosphonous acid (produced as in Example 1). Ethylene oxide is introduced at room temperature. A reaction temperature of 70° C. is set with cooling, followed by further reaction at 80° C. for one hour. The ethylene oxide takeup is 65.7 g. The acid number of the product is less than 1 mg KOH/g. Yield: 129 g (94% of theory) of 2-hydroxyethyl ethylphosphonite as colorless, water-clear product.

EXAMPLE 5

A 1 l five-neck flask equipped with thermometer, reflux condenser, high-performance stirrer and dropping funnel was initially charged with 447 g (3 mol) of butyl ethylphosphonite (produced as in Example 3) and 168 g (3 mol) of 2-propenal. While stirring, 15 ml of sodium butoxide (30% in butanol) are added dropwise at such a rate that a reaction temperature of max. 120° C. becomes established. The crude product thus obtained is distilled in vacuo to obtain 550 g (89% of theory) of butyl ethyl(2-formylethyl)phosphinate as colorless liquid.

EXAMPLE 6

A 500 ml five-neck flask equipped with thermometer, reflux condenser, high-performance stirrer and dropping funnel is initially charged with 63.5 g (0.46 mol) of 2-hydroxyethyl ethylphosponite (produced as in Example 4) and 32.2 g (0.46 mol) of 2-methyl-2-propenal. While stirring, 25 ml of sodium ethoxide (30% in ethanol) are added dropwise at such a rate that a reaction temperature of 60° C. becomes established. A slightly yellow-colored liquid is obtained. The crude product thus obtained is distilled in vacuo to obtain 84 g (88% of theory) of 2-hydroxyethyl ethyl(2-methyl-2-formylethyl)phosphinate as colorless liquid.

EXAMPLE 7

A 1 L capacity loop reactor is filled with a mixture of 801 g (4.5 mol) of ethyl ethyl-2-formylethylphosphinate (produced similarly to Example 10) and 62 g (1.35 mol) of ethanol. The pump is switched on and per hour a mixture of 726 g (6.00 mol) of ethyl ethylphosphonite (produced similarly to Example 2) and 336 g (6.00 mol) of 2-propenal and also a solution of 16.8 g (0.20 mol) of potassium ethoxide in 120 g (2.61 mol) of ethanol are metered in while the cooling water circuit was used to maintain the reaction mixture at a temperature of about 40° C. The overflowing crude product is collected for 30 hours and combined with the product drained from the reactor to produce a total amount of 35.5 kg. Following removal of the low boilers by distillation under a water jet vacuum and filtration, the product was vacuum distilled in a thin-film evaporator to obtain 30.0 kg (168.6 mol) of ethyl ethyl(2-formylethyl)phosphinate. Minus the amount initially charged to the reactor, this corresponds to a phosphorus yield of 93.8% at a rate of about 1000 g/l*h. As this example shows, a continuous production of mono-2-formyl-functionalized dialkylphosphinic esters in good space-time yields is possible.

EXAMPLE 8

564 g (6 mol) of ethylphosphonous acid (produced as in Example 1) are dissolved in 860 g of water and initially charged to a 5 l five-neck flask equipped with thermometer, reflux condenser, high-performance stirrer and dropping funnel. The reaction mixture is heated to 100° C. and 392 g (7 mol) of 2-propenal and 500 g of a 5% strength sodium peroxodisulfate solution (1.5 mol % based on 2-propenal) is added dropwise at atmospheric pressure over 1 h. Then, the water is distilled off in vacuo. The residue is taken up in tetrahydrofuran and the insoluble salts are filtered off. The solvent of the filtrate is removed in vacuo to leave 675 g (75% of theory) of ethyl(2-formylethyl)phosphinic acid as oil.

EXAMPLE 9

149 g (1 mol) of butyl ethyiphosphonite (produced as in Example 2) and 67 g (1.2 mol) of 2-propenal in 217 g of toluene are heated to about 100° C. While stirring, 124 g of a 10% strength solution of WakoV65 in toluene are added by metered addition. The solvent is distilled off in vacuo to leave 171 g (78% of theory) of butyl ethyl(2-formylethyl)phosphinate.

EXAMPLE 10

In a glass autoclave, 240 g of ethanol, 68 g of ammonia, 52 g of water, 6.4 g of Raney® nickel (doped with 1.5% by weight of chromium), 55.5 g (0.37 mol) of ethyl(2-formylethyl)phosphinic acid (produced as in Example 8) are reacted at 70° C. with hydrogen at 25 bar. Following a reaction time of 8 hours, the autoclave was let down. For purification, the reaction solution is filtered and concentrated in vacuo.

The residue obtained is taken up in 150 g of water admixed with about 30 g (0.37 mol) of 50% strength sodium hydroxide solution and subsequently neutralized by addition of about 18.1 g (0.19 mol) of concentrated sulfuric acid. The water is subsequently distilled off in vacuo. The residue is taken up in ethanol and the insoluble salts are filtered off. The solvent of the filtrate is removed in vacuo. The product is purified by chromatography to obtain 37.1 g (66% of theory) of ethyl(3-hydroxypropyl)phosphinic acid as colorless oil.

EXAMPLE 11

In a glass autoclave, 240 g of hexamethylenediamine, 52 g of water, 6.4 g of Raney® nickel (doped with 1.5% by weight of chromium), 0.18 g (4 mmol) of potassium hydroxide, 75.1 g (0.37 mol) of butyl ethyl(2-formylethyl)phosphinate (produced in as Example 9) are reacted at 50° C. with hydrogen at 25 bar. Following a reaction time of 8 hours, the autoclave was let down. For purification, the reaction solution is filtered, passed through a column charged with Deloxan® THP II and concentrated in vacuo. The product is purified by chromatography to obtain 63.9 g (83% of theory) of butyl ethyl(3-hydroxypropyl)phosphinate as colorless oil.

EXAMPLE 12

At room temperature, 2.3 g (0.06 mol) of lithium aluminohydride in 100 ml of absolute diethyl ether in a three-neck flask equipped with stirrer, dropping funnel and high-performance condenser are, while continuously stirring, admixed with a solution of 22.0 g (0.1 mol) of butyl ethyl(2-methyl-2-formylethyl)phosphinate in 100 ml of diethyl ether added dropwise at such a rate that there is a moderate boil of the diethyl ether. On completion of the dropwise addition the reaction solution is refluxed for 1 hour and subsequently admixed with 1.8 g (0.1 mol) of water. The insoluble salts are filtered off. The solvent of the filtrate is removed in vacuo and the product is purified by chromatography to obtain 18.9 g (85% of theory) of butyl ethyl(2-methyl-3-hydroxypropyl) phosphinate as colorless oil.

EXAMPLE 13

444 g (2 mol) of butyl ethyl(2-methyl-3-hydroxypropyl) phosphinate (produced as in Example 13) are initially charged to a 1 l five-neck flask equipped with thermometer, reflux condenser, high-performance stirrer and dropping funnel. At 160° C., during 4 h, 500 ml of water are metered in and a butanol-water mixture is distilled off. The solid residue is recrystallized from acetone to obtain 329 g (99% of theory) of ethyl(2-methyl-3-hydroxypropyl)phosphinic acid as oil.

EXAMPLE 14

912 g (6 mol) of ethyl(3-hydroxypropyl)phosphinic acid (produced as in Example 10) are dissolved in 860 g of water and initially charged into a 5 l five-neck flask equipped with thermometer, reflux condenser, high-performance stirrer and dropping funnel and neutralized with about 480 g (6 mol) of 50% sodium hydroxide solution. A mixture of 1291 g of a 46% aqueous solution of $Al_2(SO_4)_3.14H_2O$ is added at 85° C. The solid material obtained is subsequently filtered off, washed with hot water and dried at 130° C. in vacuo. Yield: 860 g (89% of theory) of ethyl(3-hydoxypropyl)phosphinic acid aluminum(III) salt as colorless salt.

EXAMPLE 15

166 g (1 mol) of ethyl(2-methyl-3-hydroxypropyl)phosphinic acid (produced as in Example 13) and 85 g of titanium tetrabutoxide are refluxed in 500 ml of toluene for 40 hours. The resulting butanol is distilled off from time to time with proportions of toluene. The solution formed is subsequently freed of solvent to leave 161 g (91% of theory) of ethyl(2-methyl-3-hydroxypropyl)phosphinic acid titanium salt.

EXAMPLE 16

456 g (3 mol) of ethyl-3-hydroxypropylphosphinic acid (produced as in Example 10) are at 85° C. dissolved in 400 ml of toluene and admixed with 888 g (12 mol) of butanol. At a reaction temperature of about 100° C., the water formed is removed by azeotropic distillation to obtain 524 g (84% of theory) of butyl ethyl(3-hydroxy-propyl)phosphinate purified by distillation at reduced pressure.

EXAMPLE 17

498 g (3.0 mol) of ethyl(2-methyl-3-hydroxypropyl)phosphinic acid (produced as in Example 13) are at 80° C. dissolved in 400 ml of toluene and admixed with 594 g (6.6 mol) of 1,4-butanediol and esterified at about 100° C. in a distillation apparatus equipped with water trap during 4 h. On completion of the esterification the toluene is removed in vacuo to leave 557 g (78% of theory) of 4-hydroxybutyl ethyl(2-methyl-3-hydroxypropyl)phosphinate as colorless oil.

EXAMPLE 18

To 416 g (2 mol) of butyl ethyl(3-hydroxypropyl)phosphinate (produced as in Example 11) are added 155 g (2.5 mol) of ethylene glycol and 0.4 g of potassium titanyloxalate, followed by stirring at 200° C. for 2 h. Volatiles are distilled off by gradual evacuation to leave 439 g (98% of theory) of 2-hydroxyethyl ethyl(3-hydroxypropyl)phosphinate.

EXAMPLE 19

A 500 ml five-neck flask equipped with gas inlet tube, thermometer, high-performance stirrer and reflux condenser with gas incineration is charged with 152 g (1 mol) of ethyl (3-hydroxypropyl)phosphinic acid (produced similarly to Example 13). Ethylene oxide is passed in at room temperature. A reaction temperature of 70° C. is set with cooling, followed by further reaction at 80° C. for 1 hour. The ethylene oxide takeup is 64.8 g. The acid number of the product is less than 1 mg KOH/g. 186 g (95% of theory) of 2-hydroxyethyl ethyl(3-hydroxy-propyl)phosphinate are obtained as colorless, water-clear liquid.

EXAMPLE 20

Terephthalic acid, ethylene glycol and 2-hydroxyethyl ethyl(3-hydroxy-propyl)phosphinate (produced as in Example 18) are polymerized in a weight ratio of 1000:650:70 in the presence of zinc acetate and antimony(III) oxide under the usual conditions. To 19.6 g of 2-hydroxyethyl ethyl (3-hydroxypropyl)phosphinate are added 290 g of terephthalic acid, 182 g of ethylene glycol and 0.34 g of zinc acetate, and the mixture is heated to 200° C. for 2 h. Then, 0.29 g of trisodium phosphate anhydrate and 0.14 g of antimony(III) oxide are added, followed by heating to 280° C. and subsequent evacuation.

The melt obtained (351 g, phosphorus content 0.9%) is used to injection mold test specimens 1.6 mm in thickness for measurement of the limiting oxygen index (LOI) to ISO 4589-2 and also for the UL 94 (Underwriter Laboratories) flammability test. The test specimens thus produced gave an LOI of 40% $O_2$ and were UL 94 classified as flammability class V-0. Corresponding test specimens without 2-hydroxyethyl ethyl(3-hydroxypropyl)phosphinate gave an LOI of just 31% $O_2$ and were UL 94 classified as flammability class V-2 only. The polyester molded article containing 2-hydroxyethyl ethyl(3-hydroxypropyl)phosphinate hence clearly has flame-retardant properties.

EXAMPLE 21

To 14.0 g of ethyl(2-methyl-3-hydroxypropyl)phosphinic acid (produced as in Example 13) are added to 7.6 g of 1,3-propylene glycol and at 160° C. the water formed by esterification is stripped off. Then, 378 g of dimethyl terephthalate, 152 g of 1,3-propanediol, 0.22 g of tetrabutyl titanate and 0.05 g of lithium acetate are added and the mixture is initially heated at 130 to 180° C. for 2 h with stirring and thereafter at 270° C. at underpressure. The polymer (438 g) contains 0.6% of phosphorus, the LOI is 34.

EXAMPLE 22

To 12.8 g of ethyl(3-hydroxypropyl)phosphinic acid (produced as in Example 10) are added 367 g of dimethyl terephthalate, 170 g of 1,4-butanediol, 0.22 g of tetrabutyl titanate and 0.05 g of lithium acetate and the mixture is initially heated at 130 to 180° C. for 2 h with stirring and thereafter at 270° C. at underpressure. The polymer (426 g) contains 0.6% of phosphorus, the LOI is 34, the LOI of untreated polybutylene terephthalate is 23.

EXAMPLE 23

In a 250 ml five-neck flask equipped with reflux condenser, stirrer, thermometer and nitrogen inlet, 100 g of a bisphenol A bisglycidyl ether having an epoxy value of 0.55 mol/100 g (Beckopox EP 140, from Solutia) and 21.6 g (0.13 mol) of ethyl-(2-methyl-3-hydroxypropyl)phosphinic acid (produced similarly to Example 10) are heated to not more than 150° C. with stirring. A clear melt forms after 30 min. After a further hour of stirring at 150° C., the melt is cooled down and triturated to obtain 118.5 g of a white powder having a phosphorus content of 3.3% by weight.

EXAMPLE 24

In a 2 L flask equipped with stirrer, water trap, thermometer, reflux condenser and nitrogen inlet, 29.4 g of phthalic anhydride, 19.6 g of maleic anhydride, 24.8 g of propylene glycol, 15.5 g of 2-hydroxyethyl ethyl(3-hydroxypropyl) phosphinate (produced as in Example 18), 20 g of xylene and 50 mg of hydroquinone are heated to 100° C. while stirring and with nitrogen being passed through. The heating operation is stopped when the exothermic reaction is started. After the reaction has died down, stirring is continued at about 190° C. After 14 g of water have been separated off, the xylene is distilled off and the polymer melt is cooled down. This gives 91.5 g of a white powder having a phosphorus content of 2.3% by weight.

EXAMPLE 25

A mixture of 50% by weight of polybutylene terephthalate, 20% by weight of ethyl-(3-hydroxypropyl)phosphinic acid aluminium(III) salt (produced as in Example 14) and 30% by weight of glass fibers are compounded on a twin-screw extruder (Leistritz LSM 30/34) at temperatures of 230 to 260° C. to form a polymeric molding material. The homogenized polymeric strand was hauled off, water bath cooled and then pelletized. After drying, the molding materials are processed on an injection molding machine (Aarburg Allrounder) at 240 to 270° C. to form polymeric molded articles which achieved a UL-94 classification of V-0.

EXAMPLE 26

A mixture of 53% by weight of nylon-6,6, 30% by weight of glass fibers, 17% by weight of ethyl(2-methyl-3-hydroxypropyl)phosphinic acid titanium salt (produced as in Example 15) are compounded on a twin-screw extruder (Leistritz LSM 30/34) to form polymeric molding materials. The homogenized polymeric strand was hauled off, water bath cooled and then pelletized. After drying, the molding materials are processed on an injection molding machine (Aarburg Allrounder) at 260 to 290° C. to form polymeric molded articles which achieved a UL-94 classification of V-0.

What is claimed is:

1. A method for producing monohydroxy-functionalized dialkylphosphinic acids, esters or salts by means of acroleins, comprising the steps of:

a) reacting a phosphinic acid source (I)

with olefins (IV)

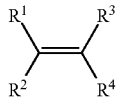

(IV)

in the presence of a catalyst A to form an alkylphosphonous acid, salt or ester (II)

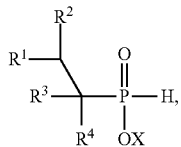

(II)

b) reacting the alkyllphosphonous acid, salt or ester (II) with an acrolein (V)

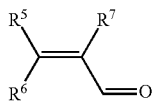

(V)

in the presence of a catalyst B to form a monofunctionalized dialkylphosphinic acid derivative (VI)

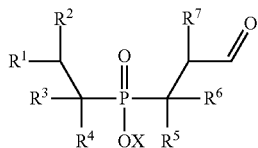

(VI)

and c) reacting the monofunctionalized dialkylphosphinic acid derivative (VI) with a reducing agent or in the presence of a catalyst C with hydrogen monohydroxy-functionalized dialkylphosphinic acid derivative (III)

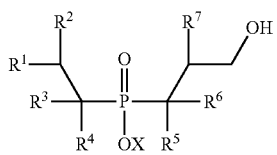

(III)

where $R^1$, $R^2$, $R^3$, $R^4$, $R^5$, $R^6$, $R^7$ are identical or different and are each independently H, $C_1$-$C_{18}$-alkyl, $C_6$-$C_{18}$-aryl, $C_6$-$C_{18}$-aralkyl, $C_6$-$C_{18}$-alkylaryl, CN, CHO, OC(O)CH$_2$CN, CH(OH)C$_2$H$_5$, CH$_2$CH(OH)CH$_3$, 9-anthracene, 2-pyrrolidone, $(CH_2)_m$OH, $(CH_2)_m$NH$_2$, $(CH_2)_m$NCS, $(CH_2)_m$NC(S)NH$_2$, $(CH_2)_m$SH, $(CH_2)_m$S-2-thiazoline, $(CH_2)_m$SiMe$_3$, C(O)R$^8$, $(CH_2)_m$C(O)R$^8$, CH=CH-R$^8$, CH=CH—C(O)R$^8$ and where $R^8$ is $C_1$-$C_8$-alkyl or $C_6$-$C_{18}$-aryl and m is an integer from 0 to 10 and X is H, $C_1$-$C_{18}$-alkyl, $C_6$-$C_{18}$-aryl, $C_6$-$C_{18}$-aralkyl, $C_6$-$C_{18}$-alkylaryl, $(CH_2)_k$OH, CH$_2$—CHOH—CH$_2$OH, $(CH_2)_k$O(CH$_2)_k$H,$(CH_2)_k$—CH(OH)—$(CH_2)_k$H, $(CH_2$—CH$_2$O)$_k$H, $(CH_2$—C[CH$_3$]HO)$_k$H, $(CH_2$—C[CH$_3$]HO)$_k$(CH$_2$—CH$_2$O)$_k$H, $(CH_2$—CH$_2$O)$_k$(CH$_2$—C[CH$_3$]HO)H, $(CH_2$—CH$_2$O)$_k$-alkyl, $(CH_2$-C[CH$_3$]HO)$_k$-alkyl, $(CH_2$—C[CH$_3$]HO)$_k$(CH$_2$—CH$_2$O)$_k$-alkyl, $(CH_2$—CH$_2$O)$_k$(CH$_2$—C[CH$_3$]HO)O-alkyl, $(CH_2)_k$—CH=CH(CH$_2)_k$H, $(CH_2)_k$NH$_2$, $(CH_2)_k$N[(CH$_2)_k$H]$_2$, where k is an integer from 0 to 10, Mg, Ca, Al, Sb, Sn, Ge, Ti, Fe, Zr, Zn, Ce, Bi, Sr, Mn, Cu, Ni, Li, Na, K, H, or a protonated nitrogen base and the catalysts A and C comprise transition metals, transition metal compounds catalyst systems composed of a transition metal or transition metal compound or a combination thereof and at least one ligand, and the catalyst B is peroxide-forming compounds, peroxo compounds, azo compounds, alkali metal hydrides, alkaline earth metal hydrides, alkai metal alkoxides, alkaline earth metal alkoxides or a combination thereof.

2. The method according to claim 1 wherein the monohydroxy-functionalized dialkylphosphinic acid, its salt or ester (III) obtained after step c) is subsequently reacted in a step d) with a metal compound, wherein the metal compound is Mg, Ca, Al, Sb, Sn, Ge, Ti, Fe, Zr, Zn, Ce, Bi, Sr, Mn, Li, Na, K or a protonated nitrogen base, or a combination thereof to form monohydroxy-functionalized dialkylphosphinic acid salts (Ill) of the metal compound or of a nitrogen compound or a combination thereof.

3. The method according to claim 1 wherein the alkylphosphonous acid, salt or ester (II) obtained after step a) and/or the monofunctionalized dialkyiphosphinic acid, salt or ester (VI) obtained after step b) and/or the monohydroxy-functionalized dialkyiphosphinic acid, salt or ester (III) obtained after step c) and/or the particular resulting reaction solution thereof are esterified with an alkylene oxide or an alcohol M-OH and/or M'-OH, and the alkylphosphonous ester (II) and/or monofunctionalized dialkylphosphinic ester (VI) and/or monohydroxy-functionalized dialkylphosphinic ester (III) are subjected to the reaction steps b) or d).

4. The method according to one or more of claims 1 wherein the groups $C_6$-$C_{18}$-aryl, $C_6$-$C_{18}$-aralkyl and $C_6$-$C_{18}$-alkylaryl are substituted with SO$_3$X$_2$, —C(O)CH$_3$, OH, CH$_2$OH, CH$_3$SO$_3$X$_2$, PO$_3$X$_2$, NH$_2$, NO$_2$, OCH$_3$, SH, OC(O)CH$_3$ or a combination thereof.

5. The method according to claim 1, wherein $R^1$, $R^2$, $R^3$, $R^4$, $R^5$, $R^6$, $R^7$ are identical or different and are each independently H, methyl, ethyl, n-propyl, isopropyl, n-butyl, isobutyl, tert-butyl, phenyl or a combination thereof.

6. The method according to claim 1, wherein Xis H, Ca, Mg, Al, Zn, Ti, Fe, Ce, methyl, ethyl, n-propyl, isopropyl, n-butyl, isobutyl, tert-butyl, phenyl, ethylene glycol, propyl glycol, butyl glycol, pentyl glycol, hexyl glycol, allyl, glycerol or a combination thereof.

7. The method according to claim 1, wherein the transition metals, transition metal compounds or a combination thereof are from the seventh and eighth transition groups.

8. The method according to claim 1, wherein the transition metals, transition metal compounds or a combination thereof include rhodium, nickel, palladium, platinum, ruthenium.

9. The method according to claim 1, wherein the catalyst B is hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-t-butyl peroxide, peroxodisulfuric acid, azobisisobutyronitrile, 2,2'-azobis(2-amidinopropane) dihydrochloride, 2,2'-azobis(N,N'-dimethyleneisobutyramidine) dihydrochloride, lithium, lithium hydride, lithium aluminohydride, methyllithium, butyllithium, t-butyllithium, lithium diisopropylamide, sodium, sodium hydride, sodium borohydride, sodium methoxide, sodium ethoxide, sodium butoxide, potassium methoxide, potassium ethoxide, potassium butoxide or a combination thereof.

10. The method according to claim 1, wherein the acrolein derivatives (V) are 2-propenal, 2-methyl-2-propenal, 2-phenyl-2-propenal, 3-phenyl-2-propenal, 2-methyl-3-phenyl-2-propenal, 2-butenal, 2-methyl-2-butenal, 2-phenyl-2-butenal, 3-methyl-2-butenal, 2-methyl-2-butenal, 2-pentenal, 2-methyl-2-pentenal, 2-phenyl-2-pentenal, 4-methyl-2-phenyl-2-pentenal, 2,2-dimethyl-4-pentenal or a combination thereof.

11. The method according to claim 1, wherein the alcohol of the general formula M-OH is linear or branched, saturated and unsaturated, monohydric organic alcohols having a carbon chain length of $C_1$-$C_{18}$ and the alcohol of the general formula M'—OH is linear or branched, saturated and unsaturated polyhydric organic alcohols having a carbon chain length of $C_1$-$C_{18}$.

\* \* \* \* \*